(12) United States Patent
Radspieler et al.

(10) Patent No.: US 7,067,703 B2
(45) Date of Patent: Jun. 27, 2006

(54) MANUFACTURE OF RETINOIDS

(75) Inventors: Alexander Radspieler, Grenzach-Wyhlen (DE); August Rüttimann, Arlesheim (CH)

(73) Assignee: DSM IP Assets B.V., TE Heerlen (NL)

( * ) Notice: Subject to any disclaimer, the term of this patent is extended or adjusted under 35 U.S.C. 154(b) by 0 days.

(21) Appl. No.: 10/494,079

(22) PCT Filed: Oct. 24, 2002

(86) PCT No.: PCT/EP02/11878

§ 371 (c)(1),
(2), (4) Date: Apr. 29, 2004

(87) PCT Pub. No.: WO03/037856

PCT Pub. Date: May 8, 2003

(65) Prior Publication Data

US 2005/0014976 A1    Jan. 20, 2005

(30) Foreign Application Priority Data

Oct. 31, 2001 (EP) ................... 01125965

(51) Int. Cl.
*C07C 45/00* (2006.01)
*C07C 47/42* (2006.01)
(52) U.S. Cl. ..................... 568/446; 568/447
(58) Field of Classification Search ............... 568/446, 568/447
See application file for complete search history.

(56) References Cited

U.S. PATENT DOCUMENTS

| 2,834,813 | A | * | 5/1958 | Oroshnik | 568/668 |
| 2,945,876 | A | * | 7/1960 | Klein | 558/27 |
| 3,013,081 | A | | 12/1961 | Dice | 260/593 |
| 4,968,844 | A | * | 11/1990 | Julia | 568/39 |
| 5,567,852 | A | | 10/1996 | Bienayme et al. | 568/378 |
| 5,929,288 | A | | 7/1999 | Ruttimann | 568/447 |
| 6,201,155 | B1 | | 3/2001 | Burdet et al. | 568/347 |
| 6,384,270 | B1 | | 5/2002 | Ancel et al. | 560/259 |

FOREIGN PATENT DOCUMENTS

| EP | 0 647 624 A1 | 4/1995 |
| EP | 0 816 334 A1 | 1/1998 |
| EP | 0 978 508 A2 | 2/2000 |
| WO | WO 00/02854 | 1/2000 |

OTHER PUBLICATIONS

Liotta et al. Pyridinium Dichromate-Induced 1,3-Oxidative Rearrangements of Enynols. ☐☐Tetrahedron Letters, 1987, vol. 28 (10) pp. 1069-1072.*

Zoller, T. and Uguen, D., "An Efficient Procedure for Preparing γ-Hydroxy α,β-Unsaturated Sulfones", Eur. J. Org. Chem., vol. 7, pp. 1545-1550 (1999).

Bienaymé, H., "The Palladium-Catalyzed 'Vinylogous Acetylenic Claisen Rearrangement': A New Vitamin A Synthesis and A Short Path to Allenic Unsaturated Carbonyls", Bull. Soc. Chim. Fr., vol. 132, pp. 696-708 (1995).

* cited by examiner

*Primary Examiner*—Sikarl A. Witherspoon
(74) *Attorney, Agent, or Firm*—Bryan Cave, LLP

(57) ABSTRACT

A process for the manufacture of retinal (I) comprises reacting a 5-(2,6,6-trimethyl-cyclohex-1-enyl)-1,4-pentadiene derivative (IIa) or a 5-(2,6,6-trimethyl-cyclohex-2-enyl)-1,4-pentadiene derivative (IIb) or a 5-(2,6,6-trimethyl-2-cyclohexen-1-ylidene)-1-pentene derivative (IIc) or a 5-(2,6,6-trimethyl-cyclohex-1-enyl)-penta-1-en-4-yne derivative (IId) or a 5-(2,6,6-trimethyl-cyclohex-2-enyl)-penta-1-en-4-yne derivative (IIe) with a 1,3-butadiene derivative H2C=C(CH3)CCH=CHOR4 (III) in the presence of a Lewis or Brönsted acid and subjecting the compound obtained in each case [(IVa), (IVb), (IVc), (IVd) or (IVe), respectively] to basic or acidic conditions to eliminate therefrom the moiety R2H and thus produce, according to the immediate precursor, retinal itself or a particular derivative thereof [(I'), (I''), (Va) or (Vb), respectively] and, where in two cases such derivative is produced featuring a triple bond [derivative (Va) or (Vb)], hydrogenating this to produce retinal (I) or the derivative (I'), respectively, and each case where a derivative (I') or (I'') has been produced, isomerizing this under basic or acidic conditions or in the presence of a metal catalyst to the desired retinal (I). The so-produced retinal is usually in the form of an isomeric mixture, normally as (9 E/Z, 13 E/Z)-retinal, and this can be isomerized according to a further inventive aspect to (all-E)-retinal by the acid-catalyzed formation of an adduct of (all-E)-retinal with hydroquinone in crystalline form. The so obtained (all-E)-retinal-hydroquinone adduct can then if desired be converted to vitamin A alcohol in the predominantly (all-E)-isomeric form by a method known per se. The novel starting materials (IIa), (IIb), (IIc), (IVl) and (IIe) represent a still further inventive aspect. Retinal is a valuable intermediate in the synthesis of further vitamin A compounds (retinoids). The retinoids, particularly vitamin A alcohol (retinol), are known to be valuable substances which promote the well-being of humans, inter alia in respect of vision, the immune system and growth, and for this reason are often used as components of multivitamin preparations and as additives for certain food- and feedstuffs.

20 Claims, No Drawings

MANUFACTURE OF RETINOIDS

This application is the National Stage of International Application No. PCT/EP02/11878, filed Oct. 24, 2002.

The present invention is concerned with a process for the manufacture of vitamin A aldehyde (retinal), a valuable intermediate in the synthesis of further vitamin A compounds (retinoids). The retinoids, particularly vitamin A alcohol (retinol), are known to be valuable substances which promote the well-being of humans, inter alia in respect of vision, the immune system and growth, and for this reason are often used as components of multivitamin preparations and as additives for certain food- and feedstuffs. The present invention further concerns novel starting materials in the aforementioned process and further process steps leading to (all-E)-vitamin A acetate.

According to the present invention there is provided a process for the manufacture of retinal, of the formula

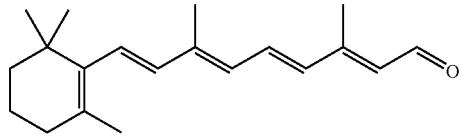

I which comprises reacting a 5-(2,6,6-trimethyl-cyclohex-1-enyl)-1,4-pentadiene derivative of the general formula

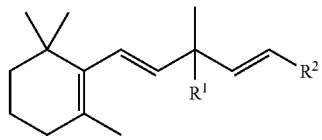

IIa or a 5-(2,6,6-trimethyl-cyclohex-2-enyl)-1,4-pentadiene derivative of the general formula

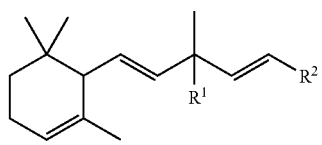

IIb or a 5-(2,6,6-trimethyl-2-cyclohexen-1-ylidene) 1-pentene derivative of the general formula

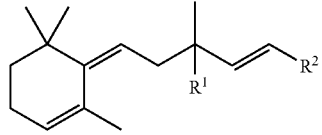

IIc or a 5-(2,6,6-trimethyl-cyclohex-1-enyl)-penta-1-en-4-yne derivative of the general formula

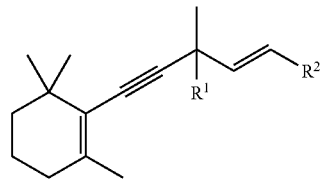

IId or a 5-(2,6,6-trimethyl-cyclohex-2-enyl)-penta-1-en-4-yne derivative of the general formula

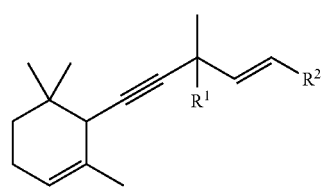

IIe wherein $R^1$ signifies hydroxyl or a group $OR^3$, $R^2$ signifies chlorine, bromine, $C_{1-6}$-alkoxy, $C_{1-6}$-alkylthio, aryloxy, arylthio, ($C_{1-6}$-alkyl)-carbonyloxy, aroyloxy, tri($C_{1-6}$-alkyl)silyloxy, di($C_{1-6}$-alkyl)phosphonyloxy, ($C_{1-6}$-alkyl)sulphonyloxy, arylsulphonyloxy, ($C_{1-6}$-alkyl)sulphonyl, arylsulphonyl, di($C_{1-6}$-alkyl)amino, N-aryl-($C_{1-6}$-alkyl)amino or diarylamino, and $R^3$ signifies $C_{1-6}$-alkyl, ($C_{1-6}$-alkyl)carbonyl, aroyl, ($C_{1-6}$-alkoxy)carbonyl, tri-($C_{1-6}$-alkyl)silyl, di($C_{1-6}$-alkyl)phosphonyl, diarylphosphonyl, ($C_{1-6}$-alkyl)sulphonyl or arylsulphonyl, with a 1,3-butadiene derivative of the general formula

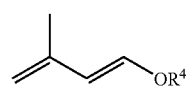

III wherein $R^4$ signifies $C_{1-6}$-alkyl, ($C_{1-6}$-alkyl)carbonyl or tri($C_{1-6}$-alkyl)silyl, in the presence of a Lewis or Brönsted acid and subjecting the so-obtained compound of the general formula

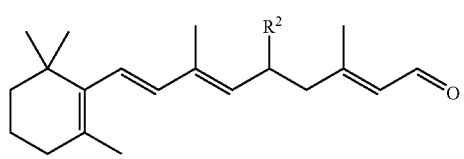

IVa (starting from the 5-substituted 1,4-pentadiene derivative of the formula IIa) or

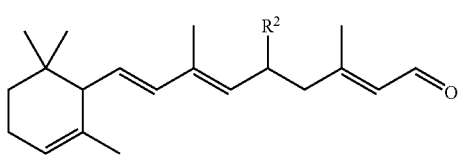
IVb (starting from the 5-substituted 1,4-pentadiene derivative of the formula IIb) or

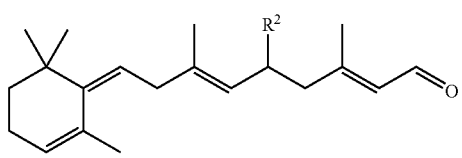
IVc (starting from the 5-substituted 1-pentene derivative of the formula IIc) or

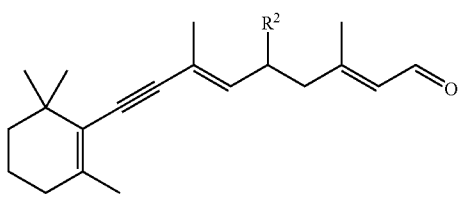
IVd (starting from the 5-substituted penta-1-en-4-yne derivative of the formula IId) or

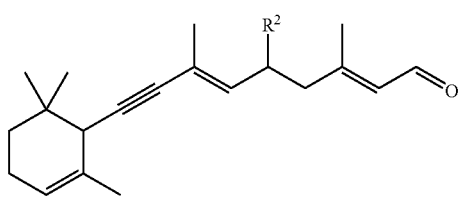
IVe (starting from the 5-substituted penta-1-en-4-yne derivative of the formula IIe)

to basic or acidic conditions to eliminate therefrom the moiety $R^2H$ and thus produce, from the compound of the formula IVa, retinal of the formula I, or, from the compound of the formula IVb, the compound of the formula

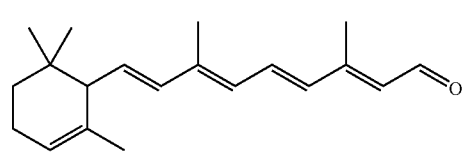
I' or, from the compound of the formula IVc, the compound of the formula

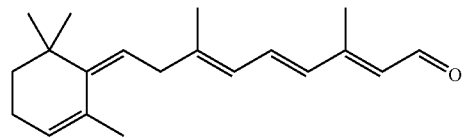
I"

or, from the compound of the formula IVd, the compound of the formula

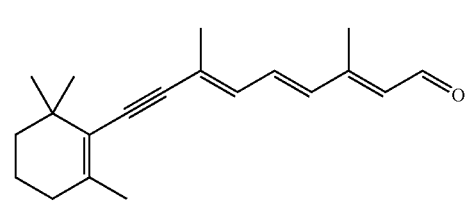
Va or, from the compound of the formula IVe, the compound of the formula

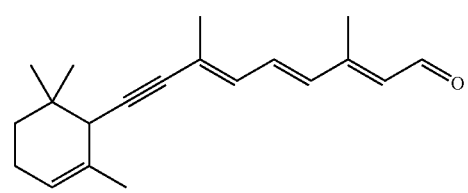
Vb and, where a compound of the formula Va or Vb has been produced, hydrogenating this to produce retinal of the formula I or the compound of the formula I' respectively, and in each case where a compound of the formula I' or I" has been produced, isomerizing this under basic or acidic conditions or in the presence of a metal catalyst to the desired retinal of the formula I.

In the above definition the term "$C_{1-6}$-alkyl" embraces (from $C_3$) straight-chain or branched alkyl groups with up to six carbon atoms, such as methyl, ethyl, isopropyl, tert. butyl, neopentyl and n-hexyl. This applies equally to the $C_{1-6}$-alkyl part of such groups as "$C_{1-6}$-alkoxy" and "$C_{1-6}$-alkylthio", and to all the bracketed $C_{1-6}$-alkyl and $C_{1-6}$-alkoxy groups. Where more than one $C_{1-6}$-alkyl group is present in a group signified by $R^2$, $R^3$ or $R^4$, e.g. in such groups as "tri($C_{1-6}$-alkyl)silyloxy", di($C_{1-6}$-alkyl)amino", "di($C_{1-6}$-alkyl)phosphonyl" or "tri($C_{1-6}$-alkyl)silyl", such $C_{1-6}$-alkyl groups may be the same or different. "Aryl" as such or as the aryl (or "ar") part of "aryloxy", "arylthio", "aroyloxy", "arylsulphonyloxy", "arylsulphonyl", "N-aryl-($C_{1-6}$-alkyl)amino", diarylamino", "aroyl" or "diarylphosphonyl" means phenyl, 1-naphthyl or 2-naphthyl, or a conventionally substituted such group, e.g. p-tolyl.

The above formulae I, I', I", IIa, IIb, IIc, IId, IIe, III, IVa, IVb, IVc, IVd, IVe, Va and Vb embrace in each case isomeric forms, e.g. optically active or inactive and E/Z-isomers, as well as mixtures thereof, unless expressly stated to the contrary. With respect to the E/Z isomerism, although the (all-E) isomeric form of the intermediate of the formula IVa, IVb, IVc, IVd, IVe, Va, Vb, I' or I" and of the product, retinal, of the formula I, is in each case preferred, each is normally present or produced, as appropriate, as a mixture of E- and Z-isomers.

In the first step of the process in accordance with the invention, i.e. the reaction of the derivative of the formula Ia, IIb, IIc, IId or IIe [hereinafter referred to for brevity as the "5-substituted pentadiene", "pentadiene", "pentene", "penta-1-en-4-yne" or "penta-1-en-4-yne" derivative, respectively [or collectively as "5-substituted pent(adi)en (yn)e"] with the 1,3-butadiene derivative under acidic conditions, an exclusive attack of the former derivative at the γ-position of the 1,3-butadiene derivative takes place.

This first process step is conveniently carried out by reacting the 5-substituted pent(adi)en(yn)e derivative of the formula IIa, IIb, IIc, IId or IIe with the 1,3-butadiene derivative of the formula III in an organic solvent at temperatures in the range of about −70° C. to about +60° C., preferably in the temperature range of about −30° C. to room temperature, and in the presence of a Lewis or Brönsted acid as the catalyst. Suitable organic solvents are, in general, polar or non-polar aprotic solvents. Such solvents are, for example, lower halogenated aliphatic hydrocarbons, e.g. methylene chloride and chloro-form; lower aliphatic and cyclic ethers, e.g. diethyl ether, tert. butyl methyl ether and tetrahydrofuran; lower aliphatic nitrites, e.g. acetonitrile; lower aliphatic esters, e.g. ethyl acetate; lower aliphatic hydrocarbons, e.g. pentane and hexane; as well as aromatic hydro-carbons, e.g. toluene. The preferred solvent is acetonitrile, optionally in combination with further aforementioned solvents. Where a mixture of acetonitrile with a further solvent is used, the ratio by volume of acetonitrile to such other solvent is preferably about 1:1 to about 1:0.5. Examples of Lewis acids which can be used are zinc chloride, zinc chloride dietherate, zinc bromide, zinc di(trifluoromethanesulphonate), titanium tetrachloride, tin tetrachloride, boron trifluoride etherate, iron(III) chloride, trimethylsilyl triflate as well as lithium perchlorate, and examples of Brönsted acids which can be used are p-toluene-sulphonic acid, methanesulphonic acid, trifluoromethanesulphonic acid, sulphuric acid as well as trifluoroacetic acid. In general, the Lewis acids, especially the aforementioned zinc salts, boron trifluoride etherate and iron(III) chloride, are preferred. The acid catalysts are in general used in catalytic (below stoichiomeric) amounts, conveniently in an amount which is 0.5 to 30 mmol percent based on the amount of 5-substituted pent(adi)en(yn)e derivative used, the mol percent range preferably being from about 1% to 15%. Where a 5-substituted pent(adi)en(yn)e derivative of the formula, IIa, IIb, IIc, IId or IIe is used in which $R^2$ signifies a basic group, in particular di($C_{1-6}$-alkyl) amino, N-aryl-($C_{1-6}$-alkyl)amino or diarylamino, a greater relative amount of acid catalyst will clearly be required, generally at least one mol equivalent. Furthermore, there are conveniently used 1.1 to 2.5 equivalents, preferably 1.1 to 1.8 equivalents, of 1,3-butadiene derivative per equivalent of 5-substituted pent(adi)en(yn)e derivative. Moreover, the reaction is conveniently effected at normal pressure. In general the pressure is not critical.

In preparing for the isolation of the product of the formula IVa, IVb, IVc, IVd or IVe, as appropriate, an acid, preferably slightly dilute aqueous acetic acid, for example featuring a ratio by volume acetic acid:water of about 9:1, may be added to the reaction mixture and the mixture is subsequently stirred for a period, for example about 30 minutes to about 2 hours, conveniently in the temperature range of about −10° C. to about 30° C. This incorporated acidification/hydrolysis step ensures that the desired intermediate of the formula IVa, IVb, IVc, IVd or IVe is finally produced from the reaction of the pent(adi)en(yn)e derivative of the formula Ia, IIb, IIc, IId or IIe with the 1,3-butadiene derivative of the formula III. The acidification/hydrolysis step is generally unnecessary, however, when the latter derivative features $R^4$ as tri($C_{1-6}$-alkyl)silyl. In any event the acidification/hydrolysis step is useful to remove excess butadiene derivative from the mixture after reaction and before the isolation of the product of the formula IVa, IVb, IVc, IVd or IVe.

The product of the formula IVa, IVb, IVc, IVd or IVe can then be isolated from the reaction mixture and, if desired, purified in a manner known per se. Typically, the mixture is combined with water and the whole is extracted with a water-immiscible organic solvent, such as, for example, a lower alkane, dialkyl ether or aliphatic ester, e.g. hexane, tert. butyl methyl ether or, respectively, ethyl acetate, and the organic phase is washed with water and/or sodium bicarbonate solution and/or saturated aqueous sodium chloride solution, dried and concentrated. The so-isolated and at least to some extent washed crude product can then, if desired, be purified further, for example by column chromatography, e.g. using silica as the stationary phase and an eluting agent such as hexane, ethyl acetate, toluene or a mixture of one or more of these.

With respect to the further (second) process step, i.e. the elimination of the compound $R^2H$ from the compound of the formula IVa, IVb, IVc, IVd or IVe, this can be effected with a base or an acid. Eliminations of the alkanol from β-alkoxyaldehydes or δ-alkoxy-α,β-unsaturated aldehydes with the formation of the corresponding α,β-unsaturated aldehydes are known in the chemical literature and can be carried out under a variety of conditions, and such methodology can be applied to the present case. For example, in the field of known base-induced eliminations 1,8-diazabicyclo[5.4.0] undec-7-ene is very often used as the base in an amount of about 1 to 2 equivalents per equivalent of aldehyde used. Such conditions are used in the known production of carotenoids [see, inter alia, Bull. Chem. Soc. Japan 50, 1161 et seq. (1977), ibid. 51, 2077 et seq. (1978), Chem. Lett. 1975, 1201 et seq. and German Offenlegungsschrift 2,701,489] and of vitamin A [see, inter alia, Chem. Lett. 1975, 1201 et seq. and J. Gen. Chem. USSR, 32, 63 et seq. (1962)]. Further methodology, using a sodium alkanolate as the base, is described in, for example, the European Patent Publications (EP) 814,078, 816,334 and 978,508. As examples of acid-induced alkanol cleavages reference is again made to Bull. Chem. Soc. Japan 50, 1161 et seq. (1977) and to J. Gen. Chem. USSR 30, 3875 et seq. (1960), in which p-toluene-sulphonic acid or 85% phosphoric acid is used as the acid catalyst. The buffer system sodium acetate/acetic acid [Helv. Chem. Acta 39, 249 et seq. and 463 et seq. (1956) and U.S. Pat. NoS. 2,827,481 and 2,827,482] has been used for such a cleavage, especially in the production of carotenoids. In the case of corresponding alkoxy ketones (β-alkoxy-ketones or δ-alkoxy-α,β-unsaturated ketones), too, the cleavage of the alkanol in general succeeds very well: see in this respect Synthesis 1986, 1004 et seq. or J. Org. Chem. 49, 3604 et seq. (1984). Taking into consideration this and other pertinent literature a person skilled in the art will have no difficulties in finding reaction conditions for the successful performance of the second step of the process in accordance with the present invention.

Furthermore, the elimination of the compound $R^2H$ can also be carried out with several equivalent amounts of a base for each equivalent of the compound of the formula IVa, IVb, IVc, IVd or IVe. Thus, the process step in this case is conveniently carried out by submitting the compound of the formula IVa, IVb, IVc, IVd or IVe, dissolved in a suitable organic solvent, to treatment with a base with elimination of the compound $R^2H$. Suitable organic solvents are, in general, protic or aprotic solvents or mixtures thereof, such as, for example, alcohols, e.g. ethanol and isopropanol, and alcohol mixtures; lower halogenated, preferably chlorinated, aliphatic hydrocarbons, e.g. methylene chloride and chloroform; and aromatic hydrocarbons, e.g. toluene. The base can be inorganic or organic, and these are suitably, in general, strong bases, especially those alkali metal alcoholates which are stronger bases, e.g. sodium ethylate, and nitrogen-containing bases, such as 1,8-diaza-bicyclo[5.4.0]undec-7-ene, trialkylamines, e.g. triethylamine, and pyridine. As indicated above, there is conveniently used at least one equivalent of base per equivalent of the compound of the formula IVa, IVb, IVc, IVd or IVe, preferably about 1 to about 2 equivalents of base.

When an alkali metal alcoholate is used as the base, either a solution of the sodium alkoxide in the alkanol is prepared in advance or this solution is prepared freshly from metallic sodium and the alkanol. The bringing together of the alkanolic solution of the sodium alkoxide with the solution or suspension of the compound of the formula IVa, IVb, IVc, IVd or IVe in the (same) alkanol, preferably likewise prepared in advance, can be effected in either sequence. The reaction mixture is then stirred, suitably in the temperature range of about −20° C. to about 120° C., preferably at temperatures of about 0° C. to about 70° C. Depending on the boiling point of the solvent the reaction is conveniently effected at normal pressure or with a slight excess pressure (In order to achieve the desired temperature). In general, however, the pressure is not critical. Under these conditions the elimination reaction is normally completed within a few hours, especially after about 30 minutes to about 4 hours.

In the case of an acid-induced elimination of the compound $R^2H$, suitable acids are, in general, strong mineral acids, such as, for example, hydrochloric acid, hydrobromic acid, hydriodic acid, sulphuric acid and perchloric acid, and sulphonic acids, such as, for example, methanesulphonic acid, trifluoromethanesulphonic acid and p-toluenesulphonic acid. The mineral acids can be aqueous and, depending on the acid, can have a concentration of about 10 to about 50%. Hydrochloric acid (especially about 10 to 37%), hydrobromic acid (especially about 25 to 63%) or hydriodic acid (e.g. 47%) is the most suitable. In this case only a catalytic amount, i.e. up to a maximum of 1 equivalent per equivalent of the compound of the formula IVa, IVb, IVc, IVd or IVe, preferably about 0.1 to about 1 equivalent, is required. Further, the acid-induced elimination is effected in a solvent in which the compound of the formula IVa, IVb) IVc, IVd or IVe has a good solubility and is dissolved therein (a so-called "homogeneous cleavage") or in a solvent in which this is not the case, i.e. in which the compound of the formula IVa, IVb, IVc, IVd or IVe is instead in suspension ("heterogeneous cleavage"). In both cases, however, the acid catalyst need not be completely dissolved. Suitable solvents for the homogenous cleavage are especially halogenated aliphatic hydrocarbons, e.g. methylene chloride, chloroform and 1,2-dichloroethane, and aromatic hydrocarbons, e.g. benzene and toluene. Suitable solvents (dispersion media) for the heterogeneous cleavage are lower aliphatic nitriles, ketones and carboxylic acids, e.g. acetonitrile, acetone and, respectively, acetic acid, preferably acetonitrile and acetone. In both cases the elimination is conveniently effected in the temperature range of about −20° C. to about +50° C., preferably in the range of about 0° C. to room temperature. The reaction time depends in each case on the reaction temperature and can amount to several hours, the elimination reaction normally being completed at the latest after about 5 hours.

Irrespective of the chosen procedure for the $R^2H$ elimination step, the product of the formula I, I', I'', Va or Vb, as appropriate, can be isolated from the reaction mixture in a manner known per se, normally by cooling the reaction mixture, conveniently to room temperature or even to about 0° C., optional addition of water and extraction with a water-immiscible organic solvent. As such a solvent there is suitably used a lower aliphatic hydrocarbon, e.g. pentane or hexane; an aromatic hydrocarbon, e.g. toluene; or a lower aliphatic ester, e.g. ethyl acetate. After its isolation the product can be purified further, if necessary or desired, by column chromatography or another conventional method for purifying retinal or an isomer or derivative thereof.

In the case where the one starting material of the process of the present invention is the 5-substituted penta-1-en-4-yne derivative of the formula IId or IIe, the product at this stage of the process, i.e. after the elimination of the moiety $R^2H$ from the compound of the formula IVd or IVe, as appropriate, is the compound of the formula Va or Vb, respectively. The next stage is the hydrogenation to produce retinal or the compound of the formula I', respectively. Said hydrogenation can be effected under catalytic hydrogenation conditions known per se, e.g. those conditions used in the analogous procedures described in Houben-Weyl, Methoden der organischen Chemie, Vol. IV/1c ("Reduktion", Teil 1), 105 et seq., Thieme Stuttgart 1980, and UK Patent Specification 722,911. The catalyst is conveniently a "poisoned" one of the Lindlar type, preferably 5% palladium on calcium carbonate poisoned with 3.5% lead, and the temperature and pressure are suitably in the range from about 5° C. to about 50° C. and about 1 to about 5 bar (about 0.1 to about 0.5 MPa), respectively. As the solvent there is suitably employed an organic solvent of relatively low polarity, e.g. an alkanol or an aliphatic ester, preferably ethyl acetate. Moreover, the (poisoned) catalyst can be advantageously modified by addition of a nitrogen-containing compound, such as quinoline.

Following the $R^2H$ elimination step, or in the aforementioned case the additional hydrogenation step, the pertinent isolated and optionally purified product, being retinal or the product of the formula I' or I'', as appropriate, is normally present as an isomeric mixture, in particular as a mixture of four isomers in respect of the 9- and 13-double bonds, said isomeric mixture being designated conventionally as the (9 E/Z, 13 E/Z) isomer.

In the case where a compound of the formula I' (starting from the 5-substituted 1,4-pentadiene or penta-1-en-4-yne derivative of the formula IIb or IIe, via the compound of the formula IVb or the compounds of the formulae IVe and Vb, respectively) is produced, or alternatively where a compound of the formula I'' (starting from the 5-substituted 1-pentene derivative of the formula IIc, via the compound of the formula IVc) is produced, the respective product is then isomerized to the desired retinal of the formula I. Conditions for the pertinent isomerization with a base, an acid or a metal catalyst are known per se and are described for example in J. Am. Chem. Soc. 108, 2090 et seq. (1986) and Chem. Ber. 118, 348 et seq. (1985) using 1,8-diazabicyclo[5.4.0]undec-7-ene and alumina in ether, respectively, as the base; in EP 647,624 and J. Chem. Res. Synop. 296 et seq. (1987) in respect of acidic conditions; and in J. Chem. Soc. Perkin Trans. 1, 1593 et seq. (1984) and Tetr. Lett. 1979, 1499 et seq. for the isomerization in the presence of the nonacarbonyl di-iron complex [$Fe_2(CO)_9$; in benzene] and the tri (triphenylphosphinyl)-rhodium chloride complex [Rh(PPh$_3$)$_3$Cl], respectively, as the metal catalyst.

If desired the so-produced retinal, predominantly in the (9 E/Z, 13 E/Z)-isomeric form, can then be isomerized to the generally desired isomeric form of retinal, (all-E)-retinal. The isomerization can be effected under conventional isomerizing conditions, and a particularly preferred method involves the acid-catalysed formation of an adduct of (principally) (all-E)-retinal with hydroquinone from the retinal produced as defined and described above, and initially in the essentially (9 E/Z, 13 E/Z)-isomeric form, and the hydroquinone in an organic solvent in which the adduct itself is sparingly soluble, thereby affording the desired (all-E)-retinal-hydroquinone adduct in crystalline form. This adduct formation represents a further aspect of the present invention. As the acid catalyst there is suitably used hydrochloric acid (especially about 37%), hydrobromic acid (48%) or hydriodic acid (47%), p-toluenesulphonic acid or elemental iodine. The molar ratio of retinal starting material: hydroquinone is suitably about 1:0.5, and the two components are conventionally brought together in an organic solvent in which the adduct itself is sparingly soluble, such as a lower aliphatic hydrocarbon, e.g. pentane or hexane; or a lower aliphatic ether, e.g. diethyl ether. The preferred solvent is diethyl ether or a mixture of said ether and hexane. On leaving the two adduct components in such a solvent with a trace amount of the acid catalyst at ambient temperature the crystallization of the (all-E)-retinal-hydroquinone adduct generally occurs after a relatively short time, e.g. about one hour. The crystalline adduct can then be readily removed from the liquid medium by filtration and if desired washed, e.g. with a solvent usable for the formation and as mentioned above, and dried, preferably at room temperature under reduced pressure. Such conventional methodology for the formation and isolation of the (all-E)-retinal-hydroquinone is described for example in U.S. Pat. No. 3,013,081 and French Patent Publications 1,288,975 and 1,291,622.

As an alternative to the prior isolation and optional purification of the retinal formed in the above defined/described two- or three-step process (not the three- or four-step process starting from the 5-(2,6,6-trimethyl-cyclohex-1-enyl)-penta-1-en-4-yne derivative of the formula IId or IIe and involving the additional hydrogenation step) of the present invention in those cases where the R$^2$H-elimination (second process step) is acid-induced and the above-described acid-catalysed retinal-hydroquinone adduct formation is intended, said second process step and the retinal-hydroquinone adduct formation step can be combined, thus avoiding the intermediate isolation and optional purification of the retinal prior to be adduct formation. In this alternative the solvent used for the acid-induced R$^2$H elimination reaction, if not one in which the adduct would readily dissolve, such as a halogenated aliphatic hydrocarbon, must be replaced, on completion of the elimination reaction, by one in which the adduct is insoluble or sparingly soluble. Such a replacement solvent is suitably a lower aliphatic hydrocarbon, e.g. pentane or hexane, or a lower aliphatic ether, e.g. diethyl ether, i.e. a solvent indicated above as being suitable for the "separate" adduct formation. The solvent replacement is suitably effected by evaporating off the "unsuitable" one under reduced pressure and adding the suitable one. Thereafter the hydroquinone is added and the procedure for crystallization and isolation of the resulting crystalline (all-E)-retinal-hydroquinone adduct effected as described above for the "separate" adduct formation.

The so-obtained (all-E)-retinal-hydroquinone adduct can be converted to the further useful end product vitamin A alcohol (retinol) in the predominantly (all-E)-isomeric form by methods known per se, for example by direct catalytic reduction with hydrogen using a ruthenium catalyst, as described in J. Molec. Catalysis 79, 117–131(1993), ibid. 66, L 27–L 31 (1991) and U.S. Pat. No. 4,906,795. This reduction can also be effected with sodium borohydride, as described in Chem. Lett. 1975, 1201 et seq., which also indicates how retinol can be converted to vitamin A acetate by acetylation with acetic anhydride in pyridine.

With the exception of the compounds of the formula IIa wherein simultaneously R$^1$ signifies hydroxyl and R$^2$ signifies arylsulphonyl, the starting 5-substituted pent(adi)en(yn)e derivatives of the formulae Ia, IIb, IIc, IId and IIe are novel compounds and constitute a still further aspect of the present invention.

Those novel starting materials of the formulae IIa, IIb and IIc can be produced using the principles from the state of the art pertinent to additions to terminal triple bonds, using as starting materials appropriate acetylenic compounds of the formulae

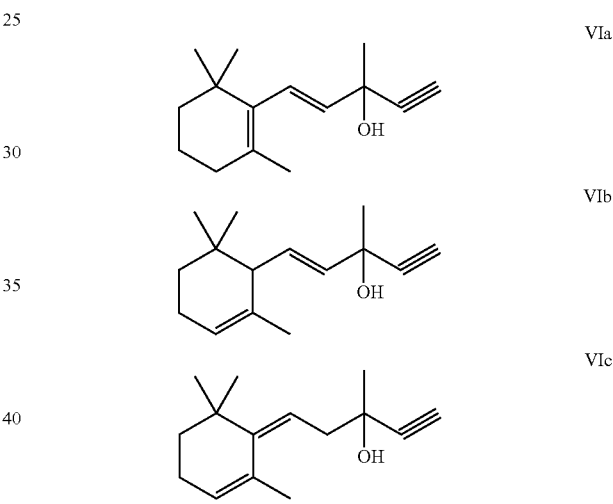

(for ultimately producing the starting materials of the formulae IIa, IIb and IIc, respectively, featuring R$^1$ as hydroxyl), or, as appropriate, the corresponding acetylenic compounds in which the group OR$^3$ is present instead of the hydroxyl group. Accordingly, the latter compounds have the following formulae VIa', VIb' and VIc':

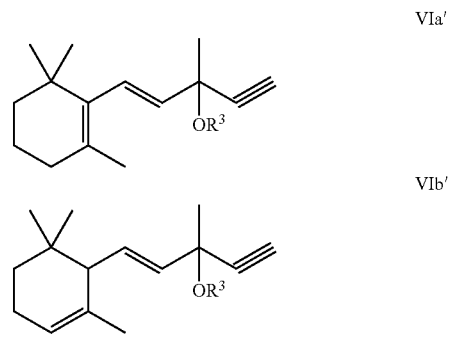

-continued

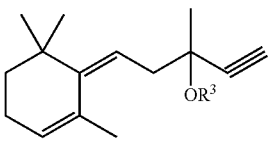

VIc' wherein $R^3$ has the pertinent significance given above, i.e. signifies $C_{1-6}$-alkyl, $(C_{1-6}$-alkyl)carbonyl, aroyl, $(C_{1-6}$-alkoxy)-carbonyl, tri$(C_{1-6}$-alkyl)silyl, di$(C_{1-6}$-alkyl)phosphonyl, diarylphosphonyl, $(C_{1-6}$-alkyl)sulphonyl or arylsulphonyl. The starting acetylenic compound of the formula VIa, VIb, VIc, VIa', VIb' or VIc' is reacted in each case with a compound supplying the $R^2$ moiety, especially the compound of the formula $R^2H$. The reaction conditions are in each case in general those employed for organometallic reactions, i.e. the use of in particular an ethereal solvent, e.g. a lower aliphatic ether, e.g. diethyl ether or dimethoxyethane, or a cyclic ether, e.g. tetrahydrofuran, and low reaction temperatures, e.g. about −100° C. to about 0° C., particularly about −70° C. to about −40° C. (see Organometallics in Synthesis, A Manual, Ed. M. Schlosser, p. 126, 1994 John Wiley & Sons Ltd.).

Examples of specific literature references providing the principles for effecting the pertinent addition reactions of such a starting acetylenic compound with a compound of the formula $R^2H$, classified according to the nature of the group $R^2$, are as follows:

$R^2$ signifies $C_{1-6}$-alkoxy: EP 274,600; Tetr. Lett. 40, 6193–6195 (1999), Synlett 7, 880 et seq. (1996) and J. Org. Chem. USSR (Engl.) 6, 903 et seq. (1970);

$R^2$ signifies $C_{1-6}$-alkylthio or arylthio: Tetr. Lett. 24, 61 et seq. (1983) and Tetr. Lett. 25, 189 et seq. (1984);

$R^2$ signifies $(C_{1-6}$-alkyl)carbonyloxy or aroyloxy: Bull. Soc. Chim. Fr. 133, 939–944 (1996), Organomet. 15, 3998–4004 (1996) and J. Organomet. Chem. 551, 151–157 (1998);

$R^2$ signifies arylsulphonyl: Tetrahedron 46, 7197–7206 (1990);

$R^2$ signifies chlorine or bromine: Org. Reactions 13, 150 et seq. (1963) and Tetr. Lett. 32, 5861–5864 (1991);

Those novel starting 5-substituted pent(adi)ene derivatives of the formulae IIa, IIb and IIc wherein $R^1$ signifies hydroxyl and $R^2$ signifies one of the previously given (selected) groups $R^2$ or signifies aryloxy, tri$(C_{1-6}$-alkyl) silyloxy, di$(C_{1-6}$-alkyl)phosphonyloxy, $(C_{1-6}$-alkyl)sulphonyloxy, arylsulphonyloxy, $(C_{1-6}$-alkyl)sulphonyl, di$(C_{1-6}$-alkyl)amino, N-aryl-$(C_{1-6}$-alkyl)amino or diarylamino can (also) be produced according to the two-step process represented schematically as follows:

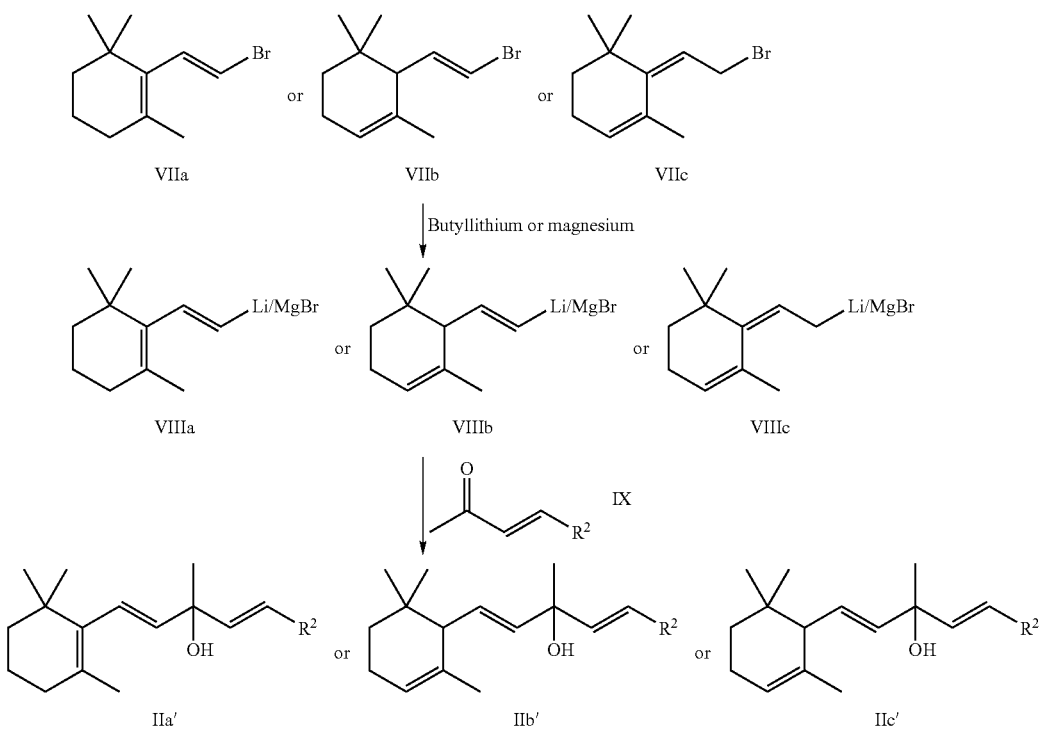

In each case the reaction conditions are generally those employed for the same type of reaction as described in the aforementioned Organometallics in Synthesis article edited by M. Schlosser, as well as in J. Org. Chem. 23, 1063 et seq. (1958) and J. Org. Chem. 43, 1595 et seq. (1978).

Those 5-substituted pent(adi)ene derivatives of the formulae IIa, IIb and IIc wherein $R^2$ signifies chlorine or bromine can also be produced by "indirect" addition of HCl or HBr, respectively, to the triple bond of the pertinent starting acetylenic compounds of the formulae VIa, VIb, VIc, VIa', VIb' and VIc' by initial addition of an organic boron compound [see, for example, J. Org. Chem. 54, 6068 et. seq. (1989), Tetr. Lett. 39, 3103–3106 (1998), Synth. Commun. 11, 247 et seq. (1981), Synth. Commun. 1983, 1027 et seq. and J. Chem. Soc. Perkin Trans. 1, 2725–2726

(1992)], an alkyl aluminium hydride [Tetr. Lett. 29, 6243 et seq. (1988)], stannic hydride [Synth. 1986, 453 et seq., J. Am. Chem. Soc. 106, 5734 et seq. (1984), Tetr. Lett. 39, 6099 et seq. (1998) and Helv. Chim. Acta 66, 1018 et seq. (1983)] or a zirconium compound [J. Org. Chem. 56, 2590 et seq. (1991), Synth. 1993, 377–379, and Tetr. Lett. 31, 7257 et seq. (1990)], followed by the halogenation of the respective intermediate product with a halogenating agent such as elemental chlorine or N-chlorosuccinimide or, respectively, elemental bromine or N-bromosuccinimide.

An alternative method for producing those 5-substituted pent(adi)ene derivatives of the formulae Ia, IIb and IIc wherein $R^1$ signifies hydroxyl and $R^2$ signifies $C_{1-6}$-alkoxy is also based upon the principles described in such literature as Organometallics in Synthesis, A Manual, Ed. M. Schlosser, p. 126, 1994 John Wiley & Sons Ltd., as well as in J. Org. Chem. 23, 1063 et seq.(1958) and J. Org. Chem. 43, 1595 et seq. (1978). According to the method β-ionone, α-ionone or retro-ionone, of the formula Xa, Xb or Xc, respectively,

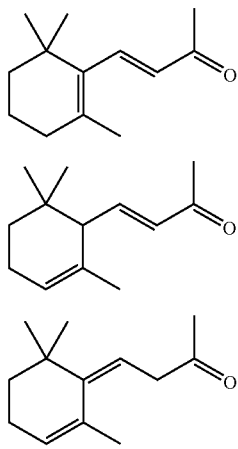

Xa

Xb

Xc is reacted with the appropriate cis-1-lithio-2-alkoxyethylene (cis LiCH=CHO$C_{1-6}$-alkyl) in an ethereal solvent at temperature of about –100° C. to about 0° C. As the ethereal solvent there is especially employed a lower aliphatic ether, e.g. diethyl ether or dimethoxyethane, or a cyclic ether, e.g. tetrahydrofuran. The reaction is preferably effected at temperature of about –70° C. to about –40° C. Furthermore, the starting cis-1-lithio-2-alkoxyethylene is conveniently prepared in situ from the corresponding cis-1-bromo-2-alkoxyethylene (cis BrCH=CHO$C_{1-6}$-alkyl) and n-butyllithium or sec. butyllithium (about equimolar amounts of the two reactants) or tert. butyllithium (In about double the molar amount relative to the amount of ethylene derivative employed) using the same solvent and reaction temperature as given above for the ensuing reaction with the so-produced 1-lithio-2-alkoxyethylene. The ultimately produced 5-substituted pent(adi)ene derivative is conveniently isolated from the mixture after completed reaction by addition of water thereto and extraction with a water-immiscible organic solvent, particularly an aprotic such solvent, such as a lower aliphatic hydrocarbon, e.g. hexane; an aromatic hydrocarbon, e.g. toluene; a lower halogenated aliphatic hydrocarbon, e.g. methylene chloride or chloroform; a lower aliphatic or cyclic ether, e.g. diethyl ether, tetrahydrofuran or dioxan; or a halogenated aromatic hydrocarbon, e.g. chlorobenzene. After removal of the extracting solvent, suitably at somewhat elevated temperature and reduced pressure, the appropriate desired 5-substituted 1-alkoxy-3-methyl-3-hydroxy-pent(adi)ene of the formula IIa, IIb or IIc is generally obtainable in good purity and in practically quantitative yield. It does not normally have to be purified further before use in the process of the present invention involving reaction with the 1,3-butadiene derivative of the formula III.

The precursors of the formulae VIa, VIb and VIc, as also the precursors of the formulae Xa, Xb and Xc, are known compounds. Literature references concerning these precursors include, for example, in respect of
precursor VIa: German Patent Publication (DE) 2,731,284;
precursor VIb: Can. J. Chem. 46, 3041 et seq. (1968); and
precursors VIc and Xc: PCT Patent Publication WO 00/002, 854 A1 and Bull. Soc. Chim. Fr. 132, 696 et seq. (1995).

The precursors of the formulae Xa and Xb are commercially available.

Only certain precursors of the formulae VIa', VIb' and VIc' are known compounds, e.g. the compounds of the formula VIa' wherein $R^3$ is methyl or ethyl (see DE 2,321,141 and U.S. Pat. No. 4,035,425); of the formula VIb' wherein $R^3$ is acetyl (see WO 00/002,854 A1); of the formula VIa' wherein $R^3$ is benzoyl [see J. Am. Chem. Soc. 102, 6355 et seq. (1980), ibid. 104, 6115 et seq. (1982), ibid. 107, 1028 et seq. (1985) and ibid. 107, 1034 et seq. (1985)]; of the formula VIb' wherein $R^3$ is methoxycarbonyl (see EP 647,624); and of the formula VIa' wherein $R^3$ is triethylsilyl [see J. Org. Chem. 63, 8704 et seq. (1998)].

The remaining precursors of the formulae VIa', VIb' and VIc' can be produced from the respective precursors of the formulae VIa, VIb and VIc by the following methods, according to the nature of the group $R^3$:

$R^3$ signifies $C_{1-6}$-alkyl: as described in DE 2,321,141 and U.S. Pat. No. 4,035,425 ($R^3$ is methyl or ethyl: see above) or analogously to the pertinent method;

$R^3$ signifies ($C_{1-6}$-alkyl)carbonyl: as described in WO 00/002,854 A1 or J. Org. Chem. 56, 5349 et seq. (1991) or analogously to the pertinent method by alkanoylation of the respective compound of the formula VIa, VIb or VIc with the appropriate carboxylic acid anhydride, e.g. acetic anhydride, in the presence of a base;

$R^3$ signifies aroyl: as described in J. Am. Chem. Soc. 102, 6355 et seq. (1980), ibid. 104, 6115 et seq.(1982), ibid. 107, 1028 et seq.(1985) or ibid. 107, 1034 et seq. (1985), or analogously to the pertinent method by aroylation of the respective compound of the formula VIa, VIb or VIc with the appropriate aromatic acid anhydride in the presence of a base;

$R^3$ signifies ($C_{1-6}$-alkoxy)carbonyl: as described in EP 647, 624 or analogously to the pertinent method by reaction of the respective compound of the formula VIa, VIb or VIc with the appropriate alkoxycarbonyl chloride in the presence of a base;

$R^3$ signifies tri($C_{1-6}$-alkyl)silyl: as described in J. Org. Chem. 63, 8704 et seq. (1998) or analogously to the pertinent method of reaction of the respective compound of the formula VIa, VIb or VIc with the appropriate trialkylsilyl chloride in the presence of a base, e.g. triethylamine or dimethylaminopyridine;

$R^3$ signifies di($C_{1-6}$-alkyl)phosphonyl or diarylphosphonyl: analogously to the pertinent method described in J. Org. Chem. 54, 627 et seq. (1989) by reaction of the respective compound of the formula VIa, VIb or VIc with an appropriate dialkyl chlorophosphite and subsequent oxidation of the so produced phosphite to the phosphate, or analogously to the pertinent method described in Tetr.

Lett. 1984, 4195 et seq. by reaction of the respective compound of the formula VIa, VIb or VIc with an appropriate dialkyl or diaryl chlorophosphate in the presence of a base.

$R^3$ signifies ($C_{1-6}$-alkyl)sulphonyl or arylsulphonyl: analogously to the pertinent method described in Synlett 1053 et seq. (1999) or Tetrahedron 55, 6387 et seq. (1999) by reaction of the respective compound of the formula VIa, VIb or VIc with an appropriate alkanesulphonic acid chloride or arylsulphonic acid chloride in the presence of a base, e.g. triethylamine or pyridine.

The precursors of the formulae VIIa, VIIb and VIIc can be produced from β-ionone, α-ionone and retro-ionone (compounds of the formulae Xa, Xb and Xc respectively, given above) by a haloform degradation reaction, in particular with bromine in aqueous sodium hydroxide according to the method described on pages 325–326 in Carotenoids Volume 2: Synthesis, Ed. G. Britton, S. Liaaen-Jensen and H. Pfander, Birkhäuser Verlag Basel Boston Berlin 1996, to afford the appropriate β-substituted acrylic acid of the formula XIa or XIb or γ-substituted vinylacetic acid of the formula XIc,

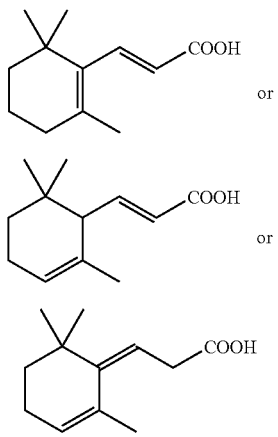

XIa

XIb

XIc respectively, followed by a Hunsdiecker reaction, e.g. with N-bromosuccinimide, according to the method described in Tetrahedron 43, 4601–4608 (1987), to produce the compound of the formula VIIa, VIIb or VIIc, respectively.

The precursors of the formula IX are in some cases known compounds and otherwise can be produced analogously to the known ones; the pertinent literature for the various types of the group $R^2$ is given hereafter:

$R^2$ signifies chlorine or bromine: J. Chem. Soc. Perkin Trans. 1990, 3317–3319;

$R^2$ signifies $C_{1-6}$-alkoxy: Collect. Czech. Chem. Commun. 1992, 1072–1080, which describes the production of the precursor of the formula IX wherein $R^2$ signifies ethoxy; the corresponding compound with $R^2$ as methoxy is commercially available.

$R^2$ signifies $C_{1-6}$-alkylthio or arylthio: J. Org. Chem. 46, 235 et seq. (1981);

$R^2$ signifies aryloxy: Fette, Seifen, Anstrichmittel 82, 82–86 (1980);

$R^2$ signifies ($C_{1-6}$-alkyl)carbonyloxy or aroyloxy: J. Org. Chem. 50, 1955–1959 (1985);

$R^2$ signifies tri($C_{1-6}$-alkyl)silyloxy: Liebigs Ann. Chem. 12, 2352 et seq. (1985);

$R^2$ signifies di($C_{1-6}$-alkyl)phosphonyloxy: Swiss Patent No. 490,016;

$R^2$ signifies ($C_{1-6}$-alkyl)sulphonyl or arylsulphonyl: Aust. J. Chem. 41, 881 et seq. (1988);

$R^2$ signifies di($C_{1-6}$-alkyl)amino, N-aryl-($C_{1-6}$-alkyl)amino or diarylamino: Org. Prep. Proced. Int. 16, 31–36 (1984).

In the case of the precursor of the formula IX wherein $R^2$ signifies ($C_{1-6}$-alkyl)sulphonyloxy or arylsulphonyloxy the compounds are novel, and no analogous methods for their production are known. However, they can be produced by reaction of 3-keto-butyraldehyde with the respective alkane- or arylsulphonyl chloride in a solvent such as tetrahydrofuran and in the presence of a base, e.g. triethylamine. J. Heterocyclic Chem. 1991, 885–890, and J. Chem. Soc. Perkin Trans. 1, 1992, 2855–2861, respectively, provide pertinent information as to the methodology.

The alternative novel starting materials for the process of the present invention, i.e. the 5-substituted penta-1-en-4-yne derivatives of the formulae IId and IIe, can be produced from the known 1-ethynyl-2,6,6-trimethyl-cyclohex-1-ene or -2-ene, respectively, of the formula

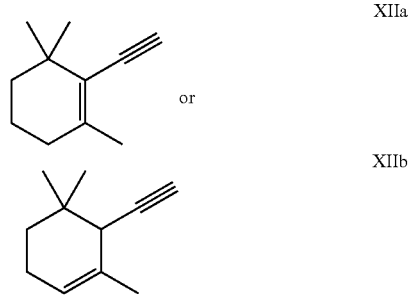

XIIa

XIIb

[(see U.S. Pat. No. 2,775,626 and Tetrahedron 55, 15071–15098 (1999), and Swiss Patent Specification 651, 287, respectively, for the production of each 1-ethynyl-2,6,6-trimethyl-cyclohexene itself] by condensation reaction under deprotonating strongly basic and anhydrous conditions with a ketone of the formula IX, given above, in an inert organic solvent. As the strong base there is suitably used a base which is customary for the deprotonation of acetylenes, especially a lithium-, sodium- or magnesium-containing base. Examples of such bases are lithium-organic compounds such as methyllithium, butyllithium or phenyllithium, Grignard reagents such as alkylmagnesium halides and dialkylmagnesium, amides such as lithium amide and sodium amide, and hydrides such as lithium hydride and sodium hydride, the preferred base being an alkyllithium or an alkylmagnesium chloride. As the solvent there is suitably used an aliphatic or cyclic ether, e.g. diethyl ether or, respectively, tetrahydrofuran or dioxan; or an aliphatic or aromatic hydrocarbon, e.g. hexane or a petroleum ether or, respectively, benzene, toluene or an xylene. The preferred solvent for the reaction is tetrahydrofuran. The ketone of formula IX is preferably used in an equivalent amount or slight excess, e.g. 1.1 to 1.3 equivalents per equivalent of the 1-ethynyl-2,6,6-trimethyl-cyclohexene of the formula XIIa or XIIb. However, a larger excess is not necessarily detrimental to the outcome of the condensation reaction. Furthermore, a slight excess of base relative to the amount of the compound of the formula XIIa or XIIb, for example about 1.1 to 1.3 equivalents, is suitably used. Moreover, it is possible to effect the condensation reaction in the additional presence of an inorganic lithium or cerium salt, which is known to slightly increase the yield of the reaction. Examples of such salts are lithium halides, cerium halides and lithium tetrafluoroborate, cerium trichloride and lithium bromide being the preferred salts. The amount of lithium or cerium salt is not critical and can amount to, for example, about 0.5 to about 2.0 equivalents per equivalent of the amount of the compound of the formula XIIa or XIIb. Regardless of the particular above-indicated conditions employed the condensation is suitably effected at temperatures from about −80° C. to about 10° C., preferably from about −70° C. to about −50° C. The condensation reaction affords those 5-substituted penta-1-en-4-yne derivatives of the formulae IId and IIe wherein $R^1$ signifies hydroxyl. The remaining 5-substituted penta-1-en-4-yne derivatives of the formulae IId and IIe, i.e. those wherein $R^1$ signifies a group $OR^3$, can be produced from the former derivatives by analogous methods for producing the precursors of the formulae VIa', VIb' and VIc' from the respective precursors of the formulae VIa, VIb and VIc, as indicated hereinabove by mention of pertinent references for the hydroxyl->$OR^3$ group transformation.

This condensation reaction affords, as indicated above, the starting 5-substituted penta-1-en-4-yne derivative of the formula IId or IIe for direct use in the process of the present invention, i.e. for reacting with the 1,3-butadiene derivative of the formula III. However, instead of such direct use, the derivative can be converted to the other employable starting material, viz. the 5-substituted 1,4-pentadiene derivative of the formula IIa or IIb, respectively, by selective reduction with a complex metal hydride, preferably a hydrido-aluminate, most preferably sodium bis(2-methoxyethoxy)aluminium hydride, under conditions described in the literature, e.g. analogous to the procedures described in Helv. Chim. Acta 73, 868–873 (1990) and U.S. Pat. Nos. 4,952,716 and 5,227,507. The reduction is conveniently carried out in an inert organic solvent, examples of such being those solvents given above in connection with the reaction of the 1-ethynyl-2,6,6-trimethyl-cyclohexene of the formula XIIa or XIIb with the ketone of the formula IX, especially the solvents referred to there as being preferred. The temperature and pressure by which the selective reduction is carried out are not critical. As the reduction proceeds rapidly, the reduction is preferably carried out at temperatures from about −50° C. to about 30° C., more preferably at temperatures from about −10° C. to about 0° C., and at atmospheric pressure. The reducing agent can be used in an about equivalent amount, or preferably in excess amount, relative to the amount of starting 5-substituted penta-1-en-4-yne derivative of the formula IId or IIe. An amount which is at least about 1.1 equivalents, for example 1.2 to 1.4 equivalents, per equivalent of said derivative is preferred. However, a larger excess is not necessarily detrimental to the outcome of the selective reduction.

The hydrolysis of the aluminium-complex, formed as the intermediate in the above-described selective reduction, to the desired 5-substituted 1,4-pentadiene derivative of the formula IIa or IIb can be effected in a manner known per se, for example, by treatment with water in the presence of an organic or inorganic acid such as p-toluenesulphonic acid, or more preferably in the presence of an alkali, such as in sodium hydroxide solution. The temperature and pressure are not critical. However, in general) the hydrolysis is carried out at atmospheric pressure and room temperature or a lower temperature, preferably at temperatures from about 0° C. to room temperature.

The 1,3-butadiene derivatives of the formula III used as starting materials in the first step of the process of the present invention are either known compounds or can be produced analogously to the known compounds, for example according to the methods described in Bull. Soc. Chim. Fr. 130 (2), 200–205 (1993), Tetr. Lett. 22 (29), 2833–2836 (1989) and ibid. 26 (47), 8591–8594 (1995).

The invention is illustrated by the following Examples:

EXAMPLE 1

Preparation of (1Z, 4E)-1-ethoxy-3-methyl-3-hydroxy-5-(2,6,6-trimethyl-cyclohex-1-enyl)-1,4-pentadiene To 750 ml of tetrahydrofuran in a 750 ml reaction flask equipped with a magnetic stirrer and argon gasification means were added under the argon atmosphere 17.6 ml (approx. 25 g, 0.16 mol) of cis-1-bromo-2-ethoxyethylene, and the mixture was then cooled to −70° C. 210 ml (0.32 mol) of tert. butyllithium (1.5 molar solution in hexane) were then slowly added to the stirred mixture under maintenance of a temperature of −70° C. to −60° C., the addition being completed within about 30 minutes. After stirring the mixture for a further 30 minutes at −70° C. a solution of 20.2 g (0.103 mol) of β-ionone (approx. 98% pure) in 60 ml of tetrahydrofutran was slowly added, maintaining the temperature of the mixture at −70° C. to −60° C. The reaction mixture was then stirred at −70° C. for 3 hours, after which the reaction was established by HPLC to have been completed.

The cooling means was removed and 200 ml of ice/water were added to the flask contents within about 10 minutes. After the mixture had reached a temperature of 0° C. it was poured into 250 ml of hexane, and the whole was washed successively with three 200 ml quantities of water and two 200 ml quantities of saturated sodium chloride solution. Then the combined aqueous phases were extracted with 250 ml of hexane. The combined hexane phases were dried over anhydrous sodium sulphate and after removal of the drying agent by filtration concentrated at 35° C. under a reduced pressure of 100–200 mbar (10–20 kPa), followed by a concentration at room temperature under high vacuum to remove the final traces of solvent. There resulted 30.25 g (quantitative yield) of (1Z, 4E)-1-ethoxy-3-methyl-3-hydroxy-5-(2,6,6-trimethyl-cyclohex-1-enyl)-1,4-pentadiene as a pale yellow oil.

$^1$H-NMR (400 MHz, CDCl$_3$): 6.05 (d, J=16 Hz, 1 H). 5.99 (d=8 Hz, 1 H), 5.54 (d, J=16 Hz, 1 H), 4.60 (d, J=8 Hz, 1 H), 3.84 (q, J~8 Hz, 2 H), 1.95 (t, J~8 Hz, 2 H), 1,65 (s, 3 H), 1.6 (m, 2 H), 1.45 (m, 2 H), 1.25 (t, J~8 Hz, 3 H), 0.98 (1s, 3 H); IR (Film, cm$^{-1}$): 1659 (C=0), 1102 (C—O—C); MS: 264.3 (M$^+$).

EXAMPLE 2

Preparation of (1Z, 4E)-1-ethoxy-3-methyl-5-(2,6,6-trimethyl-cyclohex-2-enyl)-penta-1,4-dien-3-ol Using an analogous procedure to that described in Example 1 14.32 g (92% yield) of the titled product were obtained from 10.10 g (50 mmol) of α-ionone.

$^1$H-NMR (400 MHz) CDCl$_3$): 5.96 (m, 1 H), 5.59 (d, J=12 Hz, 1 H). 5.45 (d=11 Hz, 1 H), 5.39 (m, 1 H), 4.57 (d, J=8 Hz, 1 H), 3.82 (q, J~8 Hz, 2 H), 2.13 (d, J~9 Hz, 1 H), 1,98 (s, 2 H), 1.53 (m, 2H), 1.36 (m, 3 H), 1.27 (t, J~8 Hz, 3 H),

EXAMPLE 3

Preparation of 2-(5-ethoxy-3-methoxy-3-methyl-(1E, 4Z)-penta-1,4-dienyl)-1,3,3-trimethyl-cyclohexene 0.8 ml (approx. 5.6 mmol) of potassium hydride (35% suspension in) under argon atmosphere in a 25 ml Schlenk tube equipped with a stirring bar were washed three times with hexane and decanted. After the addition of 0.72 ml (7.5 mmol) of dimethyl sulphate at ambient temperature 1.43 g (5 mmol) of (1Z, 4E)-1-ethoxy-3-methyl-5-(2,6,6-tri-methyl-cyclohex-1-enyl)-penta-1,4-dien-3-ol dissolved in 3 ml of dry tetrahydrofuran was added dropwise.

After the mixture had been stirred for 18 hours at ambient temperature, the reaction was quenched with 1.5 ml of 25%-ammonia and stirred for a further 30 minutes. The solution was then diluted with 50 ml of hexane and extracted with three 25 ml quantities of water and two 25 ml quantities of brine. The aqueous phases were re-extracted with 50 ml of hexane. The combined organic phases were concentrated under reduced pressure to yield 1.498 g (98% yield) of 2-(5-ethoxy-3-methoxy-3-methyl-(1E, 4Z)-penta-1,4-dienyl)-1,3,3-trimethyl-cyclohexene as a yellowish oil. This was sufficiently pure for further reaction.

$^1$H-NMR (400 MHz, CDCl$_3$): 6.05 (d, J=16 Hz, 1 H). 5.99 (d, J=8 Hz, 1 H), 5.48 (d, J=16 Hz, 1 H), 4.61 (d, J=7 Hz, 1 H), 3.81 (q, J=7 Hz, 2 H), 3.23 (s, 3 H), 1.97 (t, J~7 Hz, 2 H), 1,68 (s, 3 H), 1.6 (m, 2 H), 1.51 (s, 3 H), 1.45 (m, 2 H), 1.23 (t, J~8 Hz, 3 H), 0.98 (s, 6 H); IR (Film, cm$^{-1}$): 1660 (C=C), 1105 (C—O—C); MS: 278.2 (M$^+$).

EXAMPLE 4

Preparation of 3-methoxy-3-methyl-5-(2,6,6-trimethyl-cyclohex-1-enyl)-(1Z, 4E)-penta-1,4-dienyl benzoate 3.60 g (15 mmol) of 2-(3-methoxy-3-methyl-(E)-pent-1-en-4-ynyl)-1,3,3-trimethyl-cyclohexene, 2.76 g of benzoic acid) 20 ml of toluene and 90 mg (0.15 mmol) of bis-(2-methylallyl)-ethylene-bis-diphenyl-phosphine-ruthenium (II)-complex were introduced into a two-necked flask equipped with a stirring bar, a rubber septum and an argon inlet under an argon atmosphere. After stirring for 12 hours at ambient temperature the reaction mixture was heated to 45° C. for 4 hours for the completion of the reaction.

Subsequently all the volatile material was removed under a reduced pressure of 100–150 mbar (10–15 kPa) and the resulting brown oil was purified by column chromatography using 50 g of silica gel (0.04–0.063 mm) as the stationary phase and a 9:1 (v/v) mixture of hexane and ethyl acetate as the eluting agent. In this way there were obtained 2.67 g (approx. 50% yield) of 3-methoxy-3-methyl-5-(2,6,6-trimethyl-cyclohex-1-enyl)-(1Z, 4E)-penta-1,4-dienyl benzoate.

$^1$H-NMR (400 MHz, CDCl$_3$): 8.09 (d, J=7 Hz, 2 H), 7.60 (t, J=7 Hz, 1 H), 7.46 (t, J=8 Hz, 2 H), 7.38 (d, J=7 Hz, 1 H). 6.14 (d, J=16 Hz, 1 H), 5.57 (d, J=16 Hz, 1 H), 5.11 (d, J=7 Hz, 1 H), 3.28 (s, 3 H), 1.96 (t, J~6 Hz, 2 H), 1,65 (s, 3 H), 1.63 (s, 3 H), 1.57 (m, 2 H), 1.43 (m, 2 H), 0.97 (s, 3 H), 0.96 (s, 3 H); IR (Film, cm$^{-1}$): 1737 (C=O), 1667 (C=C), 1095 (C—O—C); MS: 354.2 (M$^+$).

EXAMPLE 5

Preparation of 3-hydroxy-3-methyl-5-(2,6,6-trimethyl-cyclohex-1-enyl)-(1Z. 4E)-penta-1,4-dienyl benzoate Using an analogous procedure to that described in Example 4, 9.75 g (95% yield) of 3-hydroxy-3-methyl-5-(2,6,6-trimethyl-cyclohex-1-enyl)-(1Z, 4E)-penta-1,4-dienyl benzoate were obtained from 6.60 g (30 mmol) of (E)-3-methyl-1-(2,6,6-trimethyl-cyclohex-1-enyl)-pent-1-en-4-yn-3-ol as a crude product which was sufficiently pure for further reaction.

$^1$H-NMR (400 MHz, CDCl$_3$): 8.07 (d, J=7 Hz, 2 H), 7.61 (t, J=7 Hz, 1 H), 7.47 (t, J=8 Hz, 2 H), 7.31 (d, J=7 Hz, 1 H). 6.19 (d, J=16 Hz, 1 H), 5.53 (d, J=16 Hz, 1 H), 5.22 (d, J=7 Hz, 1 H), 1.96 (t, J~6 Hz, 2 H), 1,65 (s, 6 H), 1.59 (m, 2 H), 1.45 (m, 2 H), 0.98 (s, 6 H); IR (Film, cm$^{-1}$): 1738 (C=O), 1666 (C=C); MS: 340.2 (M$^+$).

EXAMPLE 6

Preparation of 1-ethoxy-3-methyl-5-(2,6,6-trimethyl-cyclohex-2-enylidene)-(Z)-pent-1-en-3-ol Using an analogous procedure to that described in Example 1, 2.64 g (43% yield) of the titled product were obtained from 4.67 g (23.1 mmol) of retro-ionone after chromatographic purification using 30 g of silica gel (0.04–0.063 mm) as the stationary phase and a 98:2 (v/v) mixture of hexane and ethyl acetate as the eluting agent.

$^1$H-NMR (400 MHz, CDCl$_3$): 5.96 (d, J=7 Hz, 1H). 5.61 (br s, 1 H), 5.56 (t, J=7 Hz, 1 H), 4.51 (d, J=7 Hz, 1 H), 3.84 (q, J=8 Hz, 2 H), 2.70 (dd, J=18 Hz, J=7 Hz, 1 H), 2.59 (dd, J=18 Hz, J=7 Hz, 1 H), 2.06 (br s, 2 H), 1,83 (s, 3 H), 1.45 (m, 2 H), 1.36 (s, 3H), 1.28 (t, J~8 Hz, 2 H), 1.19 (s, 6 H); IR (Film, cm$^{-1}$): 1659 (C=C), 1100 (C—O—C); MS: 247.2 (M$^+$-OH).

EXAMPLE 7

Preparation of 2-(5-ethoxy-3-methyl-3-trimethylsilyloxy-(1E, 4Z)-penta-1,4-dienyl)-1,3,3-trimethyl-cyclohexene In a 100 ml Schlenk tube equipped with a stirring bar and a rubber septum 2.95 g (10 mmol) of 1-ethoxy-3-methyl-5-(2,6,6-trimethyl-cyclohex-1-enyl)-(1Z, 4E)-penta-1,4-dien-3-ol were dissolved in a mixture of 50 ml of dry dimethylformamide, 0.50 g (0.4 mmol) of 4-dimethylamino-pyridine and 7.0 ml (50 mmol) of triethylamine. The mixture was cooled to 0° C. and 5.0 ml (40 mmol) of trimethylchlorosilane was introduced dropwise.

After the mixture had been stirred for 14 hours at ambient temperature, it was diluted with 250 ml of hexane and extracted with three 250 ml quantities of water, two 250 ml quantities of saturated sodium bicarbonate solution and two 250 ml quantities of brine. The combined organic phases were dried over sodium sulphate and concentrated under reduced pressure to afford 3.49 g (93% yield) of 2-(5-ethoxy-3-methyl-3-trimethylsilyloxy-(1E, 4Z)-penta-1,4-dienyl)-1,3,3-trimethyl-cyclohexene as a yellowish oil. This was sufficiently pure for further reaction.

$^1$H-NMR (400 MHz, CDCl$_3$): 6.02 (d, J=16 Hz, 1 H). 5.81 (d, J=7 Hz, 1 H), 5.64 (d, J=16 Hz, 1 H), 4.45 (d, J=7 Hz, 1 H), 3.75 (q, J=7 Hz, 2 H), 1.97 (t, J~6 Hz, 2 H), 1,66 (s, 3 H), 1.6 (m, 2 H), 1.55 (s, 3 H), 1.40 (m, 2 H), 1.23 (t, J~7 Hz, 3 H), 0.99 (s, 6 H), 0.14 (s, 9 H); IR (Film, cm$^{-1}$): 1660 (C=C), 1105 (C—O—C); MS: 336.3 (M$^+$).

EXAMPLE 8

Preparation of trans-1-chloro-3-methyl-5-(2,6,6-trimethyl-cyclohex-1-enyl)-pent-1-en-4-yn-3-ol A solution of 1.48 g (10 mmol) of 2-ethynyl-1,3,3-trimethyl-cyclohexene in 90 ml of dry tetrahydrofuran in a 250 ml three-necked reaction flask equipped with a magnetic stirrer, a rubber septum and argon gasification means was cooled under an argon atmosphere in a dry ice bath. It was treated dropwise with 7.5 ml (12 mmol) of a 1.6 M solution of n-butyllithium in hexane as fast as the temperature could be maintained at −70 to −60° C. The addition was completed within 10 minutes. After the reaction mixture had been stirred for an additional 30 minutes at −70° C., a solution of 1.045 g (10 mmol) of 4-chloro-buten-2-one in 10 ml of dry tetrahydrofuran was added slowly. After further stirring for 3 hours at −70° C. the reaction mixture was poured into 250 ml of ice water and extracted with three 70 ml quantities of hexane. The combined organic phases were washed with three 100 ml quantities of water and 50 ml of brine, and dried over anhydrous magnesium sulphate. All the volatile material was removed under a reduced pressure of 100–200 mbar (10–20 kPa), and 2.57 g of crude product were obtained. Chromatography through 60 of silica gel (0.04–0.063 mm) with a 95:5 (v/v) mixture of hexane and ethyl acetate afforded 1.19 g (4.7 mmol, 47% yield) of the pure product.

$^1$H-NMR (400 MHz, CDCl$_3$): 6.56 (d, J=13 Hz, 1 H), 6.11 (d=13 Hz, 1 H), 2.02 (t, J=6 Hz, 2 H), 1.86 (s, 3 H), 1.63 (s, 3 H), 1.60 (m, 2 H), 1.46 (m, 2 H), 1.09 (s, 6 H) IR (Film, cm$^{-1}$): 3373 (OH), 2210 (C≡C); MS: 252.2, 254.2 (M$^+$).

EXAMPLE 9

Preparation of (1E, 4E)-1-chloro-3-methyl-5-(2,6,6-trimethyl-cyclohex-1-enyl)-penta-1.4-dien-3-ol 1.96 g (7.5 mmol) of 1-chloro-3-methyl-5-(2,6,6-trimethyl-cyclohex-1-enyl)-pent-1-en-4-yn-3-ol were dissolved in 100 ml of dry tetrahydrofuran in a 250 ml Schlenk tube equipped with a stirring bar and a rubber septum under an argon atmosphere and cooled to −10° C. 2.71 ml (9.5 mmol) of sodium-dihydrido-bis-(2-methoxyethoxy)aluminate (3.5 M in toluene) were added dropwise using a syringe. After 4 hours stirring at −10° C. the reaction mixture was quenched by adding 5 ml of a 40% solution of ethanol in hexane at 0–5° C.

For the working-up the solution was treated with 13 ml of 28% aqueous sodium hydroxide solution at 0–5° C. for 10 minutes. The resulting emulsion was diluted with 110 ml of water and extracted twice with 50 ml of hexane. The combined organic phases were extracted with five 50 ml quantities of water and 50 ml of brine, and dried over magnesium sulphate. After removal of all the volatile material at reduced pressure of 100–200 mbar (10–20 kPa) 1.94 g of crude product were obtained, which contained 94% of (1E, 4E)-1-chloro-3-methyl-5-(2,6,6-trimethyl-cyclohex-1-enyl)-penta-1,4-dien-3-ol and was sufficiently pure for further reaction.

$^1$H-NMR (400 MHz, CDCl$_3$): 6.28 (d, J=13 Hz, 1 H), 6.11 (d, J=16 Hz, 1 H), 6.09 (d=13 Hz, 1 H), 5.51 (d, J=16 Hz, 1 H), 1.97 (t, J~7 Hz, 2 H), 1.65 (s, 3 H), 1.60 (m, 2 H), 1.45 (m, 2 H), 1.44 (s, 3 H), 0.98 (s, 6 H); MS: 254.2, 256.2 (M$^+$).

EXAMPLE 10

Preparation of (9E/Z, 13 E/Z)-11,12-dihydro-11-ethoxy-retinal 12.3 g (approx. 42 mmol) of cis-1-ethoxy-3-methyl-3-hydroxy-5-(2,6,6-trimethyl-cyclohex-1-enyl)-1,4-pentadiene (approx. 90% pure), 12.5 g (80 mmol) of 1-trimethylsilyloxy-3-methyl-1,3-butadiene and 60 ml of acetonitrile were introduced into a 100 ml two-necked reaction flask equipped with a magnetic stirrer and argon gasification means. The mixture was cooled to −30° C. and 550 mg (approx. 4 mmol) of anhydrous zinc chloride were added with stirring under the argon atmosphere. The reaction mixture was stirred successively for 1 hour at −30° C., 1 hour at 0° C. and 1 hour at room temperature, after which it was established by HPLC that the reaction had been completed to about 90%.

For the working-up 10 ml of a 9:1 mixture of glacial acetic acid and water were added to the stirred mixture at room temperature, and the mixture was stirred at this temperature for a further 30 minutes. The resulting solution was added to 100 ml of water and the aqueous solution extracted with two 200 ml quantities of hexane and the combined separated organic phases washed successively with three 100 ml quantities of water and three 100 ml quantities of saturated sodium chloride solution. The separated hexane phase was dried over anhydrous sodium sulphate and, after removal of the drying agent by filtration, concentrated at 35° C. under a reduced pressure of 100–200 mbar (10–20 kPa). There resulted 15.6 g of crude product as an oil, which was then purified by column chromatography using 400 g of silica gel (0.04–0.063 mm) as the stationary phase and a 9:1 (v/v) mixture of hexane and ethyl acetate as the eluting agent. In this way there were obtained 8.84 g (approx. 64% yield) of pure (9 E/Z, 13 E/Z)-11,12-dihydro-11-ethoxy-retinal as a yellow oil.

HPLC: Constitution of retinal isomers: 4.8% (9,13-di-cis), 7.4% (13-cis), 28.0% (9-cis) and 56.7% (all-E)[total 96.9 area percent (%)]; $^1$H-NMR (400 MHz, CDCl$_3$): inter alia 4 doublets (CHO) at approx. 9.85–10 (J~8 Hz); MS: 247.2 (M$^+$); IR (Film, cm$^{-1}$): 1676 (CH=O), 1633 (C=C), 1082 (C—O—C); UV (Cyclohexane): 232 nm ($\Sigma$=49,100, log $\Sigma$=4.69).

EXAMPLE 11

Preparation of (2 E/Z 8 E/Z)-5-ethoxy-3,7-dimethyl-9-(2,6,6-trimethyl-cyclohex-2-enyl)-nona-2,6,8-trienal Using an analogous procedure to that described in Example 10, 1.495 g (4.5 mmol, 59% yield) of (2 E/Z, 6 E, 8 E/Z)-5-ethoxy-3,7-dimethyl-9-(2,6,6-trimethyl-cyclohex-2-enyl)-nona-2,6,8-trienal were obtained from 2.145 g (7.7 mmol) of (1Z, 4E)-1-ethoxy-3-methyl-5-(2,6,6-trimethyl-cyclohex-2-enyl)-penta-1,4-dien-3-ol.

HPLC: Constitution of retinal isomers: 4.7% (9,13-di-cis), 7.9% (13-cis), 23.9% (9-cis) and 61.7% (all-E) [total 95.2 area percent (%)]; $^1$H-NMR (400 MHz, CDCl$_3$): inter alia 4 doublets (CHO) at approx. 9.85–10 (J~8 Hz); MS: 330.2 (M$^+$); IR (Film, cm$^{-1}$): 1676 (CH=O), 1633 (C=C), 1082 (C—O—C);

EXAMPLE 12

Preparation of (9E/Z, 13 E/Z)-11,12-dihydro-11-benzoyloxy-retinal

Using an analogous procedure to that described in Example 10, 970 mg (2.4 mmol, 48% yield) of (9E/Z, 13 E/Z)-11,12-dihydro-11,12-benzoyloxy-retinal were obtained from 1.87 g (5.0 mmol) of 3-methoxy-3-methyl-5-(2,6,6-trimethyl-cyclohex-1-enyl)-(1Z, 4E)-penta-1,4-dienyl benzoate.

HPLC: Constitution of retinal isomers: 4.3% (9,13-dicis), 8.5% (13-cis), 34.2% (9-cis) and 46.8% (all-E) $^1$H-NMR (400 MHz, CDCl$_3$): inter alia 4 doublets (CHO) at approx. 9.85–10 (J~8 Hz); MS: 406.3 (M$^+$); IR (Film, cm$^{-1}$): 1718(CO=O), 1677 (CH=O).

(9E/Z, 13 E/Z)-11,12-dihydro-11-benzoyloxy-retinal (266 mg, 52% yield) was also obtained from 935 mg (2.5 mmol) of 3-hydroxy-3-methyl-5-(2,6,6-trimethyl-cyclohex-1-enyl)-(1Z, 4E)-penta-1,4-dienyl benzoate and 380 mg (3.75 mmol) of 1-methoxy-3-methyl-1,3-butadiene under analogous conditions.

HPLC: Constitution of retinal isomers: 3.9% (9,13-dicis), 2.2% (13-cis), 28.0% (9-cis)and 54.4% (all-E).

EXAMPLE 13

Preparation of 5-ethoxy-3,7-dimethyl-9-(2,6,6-trimethyl-cyclohex-2-enylidene)-(2E/Z, 6 E/Z)-nona-2,6-dienal Using an analogous procedure to that described in Example 10, 1.404 g (4.3 mmol, 47.2% yield) of 5-ethoxy-3,7-dimethyl-9-(2,6,6-trimethyl-cyclohex-2-enylidene)-(2E/Z, 6 E/Z)-nona-2,6-dienal were obtained from 2.380 g (9.0 mmol) of 1-ethoxy-3-methyl-5-(2,6,6-trimethyl-cyclohex-2-enylidene)-(Z)-pent-1-en-3-ol.

HPLC: Constitution of isomers: 5.1%, 9.8%, 23.2% and 52.7% (all-E)(total 95.1 area percent (%)]; $^1$H-NMR (400 MHz, CDCl$_3$): inter alia 4 doublets (CHO) at approx. 9.85–10 (J~8 Hz); MS: 330.5 (M$^+$); IR (Film, cm$^{-1}$): 1675 (CH=O), 1633 (C=C), 1083 (C—O—C).

EXAMPLE 14

Preparation of (9E, 13E)-5-chloro-3,7-dimethyl-9-(2,6,6-trimethyl-cyclohex-1-enyl)-nona-2,6-dien-8-ynal Using an analogous procedure to that described in Example 10, 325 mg (1.0 mmol, 78% yield) of (9E, 13E)-5-chloro-3,7-dimethyl-9-(2,6,6-trimethyl-cyclohex-1-enyl)-nona-2,6-dien-8-ynal were obtained from 330 mg (1.3 mmol) of 1-chloro-3-methyl-5-(2,6,6-trimethyl-cyclohex-1-enyl)-pent-1-en-4-yn-3-ol.

$^1$H-NMR (400 MHz, CDCl$_3$): 9.99 (d, J=8 Hz, 1 H), 6.39 (d, J=13 Hz, 1 H), 5.93 (d=8 Hz, 1 H), 5.87 (d, J=13 Hz, 1 H), 2.49 (d, J=13 Hz, 1 H), 2.41 (d, J=13 Hz, 1 H), 2.26 (s, 3 H), 2.00 (t, J~6 Hz, 2 H), 1.82 (s, 3 H), 1.59 (m, 2 H), 1.45 (m, 2 H), 1.43 (s, 3 H), 1.06 (s, 6 H); IR (Film, cm$^{-1}$): 2211 (C≡C), 1676 (C=O); MS: 318.2, 320.2 (M$^+$).

EXAMPLE 15

Preparation (9E/Z, 13 E/Z)-11,12-dihydro-11-chloro-retinal

Using an analogous procedure to that described in Example 303 mg (0.9 mmol, 24.4% yield) of (9E/Z, 13 E/Z)-11,12-dihydro-11-chloro-retinal were obtained from 1.21 g (3.9 mmol) of (1E, 4E)-1-chloro-3-methyl-5-(2,6,6-trimethylcyclohex-1-enyl)-penta-1,4-dien-3-ol.

$^1$H-NMR (400 MHz, CDCl$_3$): inter alia 4 doublets (CHO) at approx. 9.85–10 (J~8 Hz); MS: 320.2 (M$^+$).

EXAMPLE 16

Preparation of (9 E/Z, 13 E/Z)-retinal

To 2.48 g (7.5 mmol) of 11,12-dihydro-11-ethoxy-retinal in 22 ml of toluene in a 25 ml two-necked reaction flask equipped with a magnetic stirrer and argon gasification means were added 2.40 g (approx. 15 mmol) of 1,8-diazabicyclo[5.4.0]undec-7-ene, and the reaction mixture was stirred for 3 hours at 70° C. (according to HPLC and thin layer chromatographic analysis the elimination of ethanol had been completed at that stage). The resulting solution was then poured into 50 ml of 10% aqueous sulphuric acid and the whole extracted with two 100 ml quantities of hexane, and the combined organic phases were washed successively with 50 ml of 10% aqueous sulphuric acid, three 100 ml quantities of water, two 50 ml quantities of saturated sodium bicarbonate solution and finally two 50 ml quantities of sodium chloride solution. After drying of the separated organic phase over anhydrous sodium sulphate, and concentration at 35° C. under a reduced pressure of 100–200 mbar (10–20 kPa) there were obtained 2.42 g of crude retinal as a E/Z-isomeric mixture. Chromatography though 60 g of silica gel (0.04–0.063 mm) with a 9:1 (v/v) mixture of hexane and ethyl acetate afforded 1.81 g (85% yield) of pure retinal (E/Z-isomeric mixture) as a viscous red oil.

HPLC: Constitution of retinal isomers: 6.8% (9,13-dicis), 19.5% (13-cis), 20.1% (9-cis) and 52.7% (all-E) (total 99.1%); $^1$H-NMR (400 MHz, CDCl$_3$) inter alia 4 doublets (CHO) at 10.1–10.2 (J~8 Hz); IR (Film, cm$^{-1}$): 1661 (CH=O), 1580 (C=C conjugated); MS: 284.2 (M$^+$); UV (Cyclohexane): 367 (Σ=69,400, log Σ=4.84).

EXAMPLE 17

Preparation of (9 E/Z, 13 E/Z)-retinal from 5-ethoxy-3,7-dimethyl-9-(2,6,6-trimethyl-cyclohex-2-enylidene)-(2E/Z, 6 E/Z)-nona-2,6-dienal To a solution of 350 mg (1.0 mmol) of 5-ethoxy-3,7-dimethyl-9-(2,6,6-trimethyl-cyclohex-2-enylidene)-(2E/Z, 6 E/Z)-nona-2,6-dienal in 6 ml of acetone under argon atmosphere in a 10 ml Schlenk tube, 0.05 ml of 48% hydrobromic acid were added at −10° C. After the reaction mixture had been stirred for 1 hour at ambient temperature it was transferred into a separation funnel, diluted with 50 ml of hexane and extracted with four 25 ml quantities of water and two 25 ml quantities of brine. The organic phase was dried over sodium sulphate and concentrated under reduced pressure. 456 mg of crude product were purified by column chromatography through 8 g of silica gel (0.04–0.063 mm) with a 98:2 (v/v) mixture of hexane and ethyl acetate and afforded 139 mg (49% yield) of pure retinal (E/Z-isomeric mixture) as a viscous red oil.

EXAMPLE 18

Preparation of (all-E)-retinal-Hydroquinone Adduct 2.60 g (9.14 mmol) of (9 E/Z, 13 E/Z)-retinal (the purified product of Example 3) and 0.514 g (4.57 mmol) of hydroquinone in 6 ml of diethyl ether were introduced into a 50 ml reaction flask equipped with a magnetic stirrer and argon gasification means. A trace amount, i.e. approx. 5–10 μl, of 55% aqueous iodic acid was added to the reaction mixture under argon. After about 1 hour crystallization of the formed adduct occurred, such that the flask contents consisted of an unstirrable mass of crystals. After about 16 hours under argon the crystalline mass was supplemented with 25 ml of hexane, and the resulting suspension was stirred at room temperature for two hours. Then the crystals were collected by filtration, washed with hexane and dried under high vacuum at room temperature, affording 2.27 g (84% yield) of ochre-coloured (all-E)-retinal-hydroquinone adduct with an approximate retinal: hydroquinone ratio of 8:1 (according to $^1$H-NMR).

$^1$H-NMR (400 MHz, CDCl$_3$): 10.10 (doublet; J~8 Hz, $^1$H, CHO); HPLC: Constitution of retinal isomers: 3.0% (13-cis), 95.3% (all-E) (hydroquinone not included; total 98.3%).

EXAMPLE 19

Preparation of (all-E)-retinal-Hydroquinone Adduct From (9 E/Z, 13 E/Z)-11,12-dihydro-11-ethoxy-retinal In a 10 ml reaction flask equipped with a magnetic stirrer and argon gasification means 992 mg (3 mmol) of (9 E/Z, 13 E/Z)-11,12-dihydro-11-ethoxy-retinal were introduced into 5 ml of methylene chloride. After addition of a trace amount, i.e. approx. 5–10 μl, of 55% aqueous hydriodic acid the reaction mixture was warmed to 40° C. for 1 hour. After this time it was established from HPLC that the ethanol elimination had been completed.

The methylene chloride solvent was then removed by evaporation under reduced pressure and replaced with 1 ml of diethyl ether. 170 mg (approx. 1.5 mmol) of hydroquinone were then added and the mixture was stirred at room temperature. Thereafter, a few crystals of the desired adduct from a previously prepared batch were added, followed by 7 ml of hexane, introduced slowly, into the dark solution/suspension for promoting the crystallization. The resulting precipitate was removed by filtration, washed with hexane and dried under high vacuum. In this way there were obtained 348 mg (38% yield) of ochre-coloured (all-E)-retinal-hydroquinone adduct with a retinal: hydroquinone ratio of about 4:1.

Constitution of retinal isomers: 3.1% (13-cis), 95.3% (all-E) (total 98.4%).

What is claimed is:

1. A process for the manufacture of retinal, of the formula

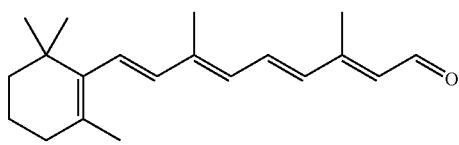

I comprising reacting a 5-(2,6,6-trimethyl-cyclohex-1-enyl)-1,4-pentadiene derivative of the general formula

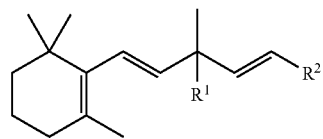

IIa or a 5-(2,6,6-trimethyl-cyclohex-2-enyl)-1,4-pentadiene derivative of the general formula

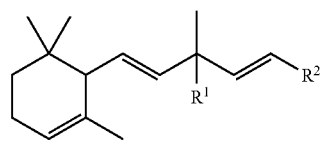

IIb or a 5-(2,6,6-trimethyl-2-cyclohexen-1-ylidene)-1-pentene derivative of the general formula

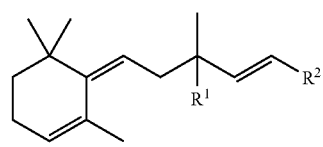

IIc or a 5-(2,6,6-trimethyl-cyclohex-1-enyl)-penta-1-en-4-yne derivative of the general formula

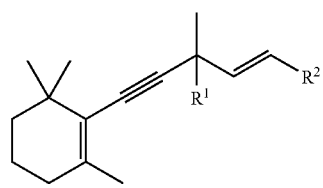

IId or a 5-(2,6,6-trimethyl-cyclohex-2-enyl)-penta-1-en-4-yne derivative of the general formula

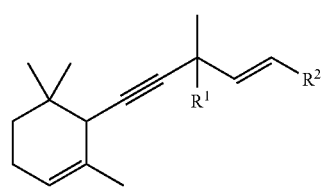

IIe wherein
R$^1$ signifies hydroxyl or a group OR$^3$,
R$^2$ signifies chlorine, bromine, C$_{1-6}$-alkoxy, C$_{1-6}$-alkylthio, aryloxy, aryithio, (C$_{1-6}$-alkyl)carbonyloxy, aroyloxy, tri(C$_{1-6}$-alkyl)silyloxy, di(C$_{1-6}$-alkyl)phosphonyloxy, (C$_{1-6}$-alkyl)sulphonyloxy, arylsulphonyloxy, ($C_{1-6}$-alkyl)sulphonyl, arylsulphonyl; di($C_{1-6}$-alkyl)amino, N-aryl-($C_{1-6}$-alkyl)amino or diarylamino, and
$R^3$ signifies $C_{1-6}$-alkyl, ($C_{1-6}$-alkyl)carbonyl, aroyl, ($C_{1-6}$-alkoxy)carbonyl, tri-($C_{1-6}$-alkyl)silyl, di($C_{1-6}$-alkyl)phosphonyl, diarylphosphonyl, ($C_{1-6}$-alkyl)sulphonyl or arylsulphonyl,
with a 1,3-butadiene derivative of the general formula

III wherein $R^4$ signifies $C_{1-6}$-alkyl, ($C_{1-6}$-alkyl)carbonyl or tri($C_{1-6}$-alkyl)silyl, in the presence of a Lewis or Brönsted acid and subjecting the so-obtained compound of the general formula IVa (starting from the 5-substituted 1,4-pentadiene derivative of the formula IIa) or IVb (starting from the 5-substituted 1,4-pentadiene derivative of the formula IIb) or IVc (starting from the 5-substituted 1-pentene derivative of the formula IIc) or IVd (starting from the 5-substituted penta-1-en-4-yne derivative of the formula IId) or IVe (starting from the 5-substituted penta-1-en-4-yne derivative of the formula IIe) to basic or acidic conditions to eliminate therefrom the moiety $R^2H$ and thus produce, from the compound of the formula IVa, retinal of the formula I, or, from the compound of the formula IVb, the compound of the formula

I' or, from the compound of the formula IVc, the compound of the formula

I'' or, from the compound of the formula IVd, the compound of the formula

Va or, from the compound of the formula IVe, the compound of the formula

Vb and, where a compound of the formula Va or Vb has been produced, hydrogenating this to produce retinal of the formula I or the compound of the formula I' respectively, and in each case where a compound of the formula I' or I" has been produced, isomerizing this under basic or acidic conditions or in the presence of a metal catalyst to the desired retinal of the formula I.

2. A process for the manufacture of retinal, of the formula

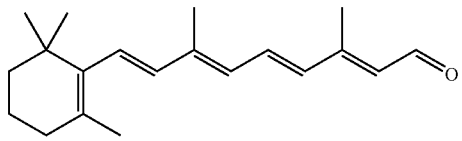

I comprising reacting a 5-(2,6,6-trimethyl-cyclohex-1-enyl)-1,4-pentadiene derivative of the general formula

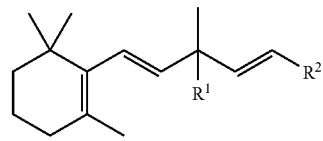

IIa or a 5-(2,6,6-trimethyl-cyclohex-2-enyl)-1,4-pentadiene derivative of the general formula

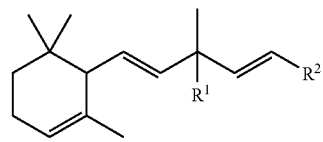

IIb or a 5-(2,6,6-trimethyl-2-cyclohexen-1-ylidene)-1-pentene derivative of the general formula

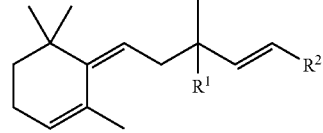

IIc wherein
R$^1$ signifies hydroxyl or a group OR$^3$,
R$^2$ signifies chlorine, bromine, C$_{1-6}$-alkoxy, (C$_{1-6}$-alkylthio, aryloxy, arylthio, (C$_{1-6}$-alkyl)carbonyloxy, aroyloxy, tri(C$_{1-6}$-alkyl)silyloxy, di(C$_{1-6}$-alkyl)phosphonyloxy, (C$_{1-6}$-alkyl)sulphonyloxy, arylsulphonyloxy, (C$_{1-6}$-alkyl)sulphonyl, arylsulphonyl, di(C$_{1-6}$-alkyl)amino, N-aryl-(C$_{1-6}$-alkyl)amino or diarylamino, and
R$^3$ signifies hydrogen, C$_{1-6}$-alkyl, (C$_{1-6}$-alkyl) carbonyl, aroyl, (C$_{1-6}$-alkoxy)carbonyl, tri-(C$_{1-6}$-alkyl)silyl, di(C$_{1-6}$-alkyl)phosphonyl, diarylphosphonyl, (C$_{1-6}$-alkyl)sulphonyl or arylsulphonyl, with a 1,3-butadiene derivative of the general formula

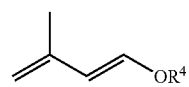

III wherein R$^4$ signifies C$_{1-6}$-alkyl, (C$_{1-6}$-alkyl)carbonyl or tri(C$_{1-6}$-alkyl)silyl, in the presence of a Lewis or Brönsted acid and subjecting the so-obtained compound of the general formula

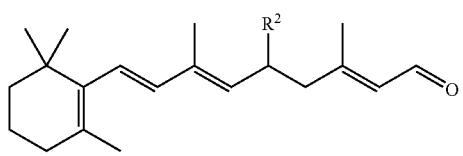

IVa (starting from the 5-substituted 1,4-pentadiene derivative of the formula IIa) or

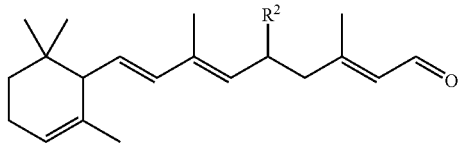

IVb (starting from the 5-substituted 1,4-pentadiene derivative of the formula IIb) or

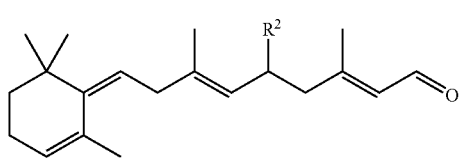

IVc (starting from the 5-substituted 1-pentene derivative of the formula IIc) to basic or acidic conditions to eliminate therefrom the moiety R$^2$H and thus produce retinal of the formula I, or, from the compound of the formula IVb, the compound of the formula

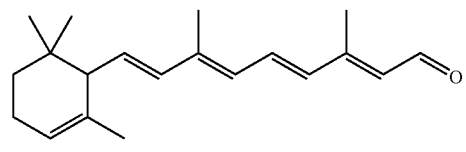

I' or, from the compound of the formula IVc, the compound of the formula,

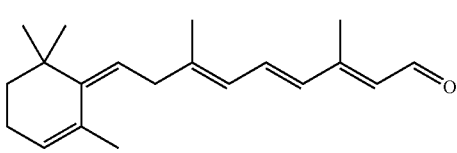

and, where a compound of the formula I' or I" has been produced, isomerizing this under basic or acidic conditions or in the presence of a metal catalyst to the desired retinal of the formula I.

3. A process according to claim 1, wherein the Lewis acid is selected from the group consisting of zinc chloride, zinc chloride dietherate, zinc bromide, zinc di(trifluoromethanesulphonate), titanium tetrachloride, tin tetrachloride, boron trifluoride etherate, iron(III) chloride, trimethylsilyl triflate and lithium perchlorate and the Brönsted acid is selected from the group consisting of p-toluenesulphonic acid, methanesulphonic acid, trifluoromethanesulphonic acid, sulphuric acid and trifluoroacetic acid.

4. A process according to claim 3, wherein a Lewis acid is selected from the group consisting of the named zinc salts, boron trifluoride etherate and iron(III) chloride.

5. A process according to claim 1, wherein the Lewis or Brönsted acid is used in a catalytic amount which is 0.5 to 30 mol percent, based on the amount of 5-substituted pent(adi)en(yn)e derivative of the formula IIa, IIb, IIc, IId or IIe used.

6. A process according to claim 1, wherein 1.1 to 2.5 equivalents, of 1,3-butadiene derivative of the formula III are used per equivalent of 5-substituted pent(adi)en(yn)e derivative of the formula IIa, IIb, IIc, IId or IIe.

7. A process according to claim 1, wherein the 5-substituted pent(adi)en(yn)e derivative of the formula IIa, IIb, IIc, IId or IIe is reacted with the 1,3-butadiene derivative of the formula III in an organic solvent at temperatures in the range of about −70° C. to about +60° C., a lower halogenated aliphatic hydrocarbon a lower aliphatic or cyclic ether; a lower aliphatic nitrile; a lower aliphatic ester; a lower aliphatic hydrocarbon; or an aromatic hydrocarbon, being used as the organic solvent.

8. A process according to claim 1, wherein in the elimination of the compound $R^2H$ from the compound of the formula IVa, IVb, IVc, IVd or IVe there is used as the base an alkali metal alcoholate, a nitrogen-containing base, a trialkylamine, or pyridine, or as the acid a strong mineral acid, or a sulphonic acid.

9. A process according to claim 1, wherein the so-produced retinal as an isomeric mixture, is isomerized to (all-E)-retinal by the acid-catalysed formation of an adduct of (all-E)-retinal with hydroquinone, said formation being effected under acid catalysis and in an organic solvent in which the adduct itself is sparingly soluble, thereby affording the desired (all-E)-retinal-hydroquinone adduct in crystalline form.

10. A process according to claim 9, wherein in the case where the $R^2H$-elimination (second process step) from the compound of the formula IVa, IVb or IVc is acid-induced and the acid-catalyzed retinal-hydroquinone adduct formation is intended said second process step and the retinal-hydroquinone adduct formation are combined, thus avoiding an intermediate isolation and optional purification of the retinal prior to the adduct formation, whereby the solvent used for the acid-induced $R^2H$ elimination reaction, if not one in which the adduct would readily dissolve, is replaced on completion of the elimination reaction by one in which the adduct is insoluble or sparingly soluble, the hydroquinone is then added and the process for formation and crystallization of the (all-E)-retinal-hydroquinone adduct is effected.

11. A process according to claim 9, wherein the so obtained (all-E)-retinal-hydroquinone adduct is converted to vitamin A alcohol in the predominantly (all-E)-isomeric form by known methods.

12. A 5-substituted pent(adi)en(yn)e derivative of the general formula

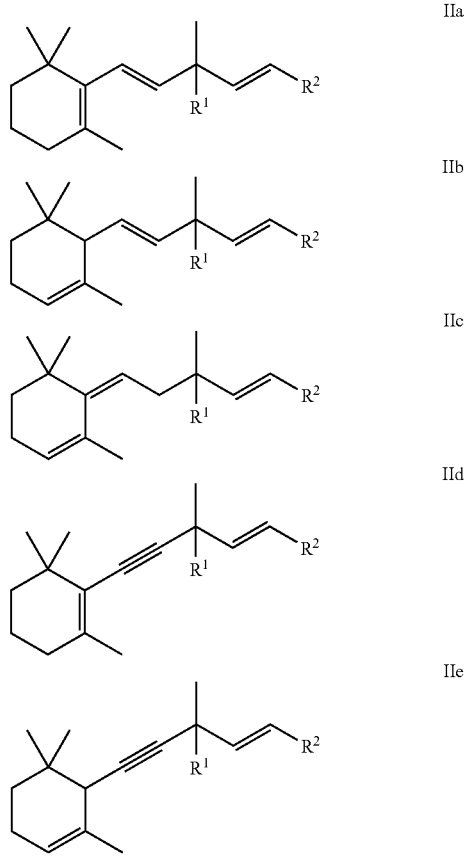

wherein $R^1$ signifies hydroxyl or a group $OR^3$, $R^2$ signifies chlorine, bromine, $C_{1-6}$-alkoxy, $C_6$-alkylthio, aryloxy, arylthio, ($C_{1-6}$-alkyl)carbonyloxy, aroyloxy, tri($C_{1-6}$-alkyl)silyloxy, di($C_{1-6}$-alkyl)phosphonyloxy, ($C_{1-6}$-alkyl)sulphonyloxy, arylsulphonyloxy, ($C_{1-6}$-alkyl)sulphonyl, arylsulphonyl, di($C_{1-6}$-alkyl)amino, N-aryl-($C_{1-6}$-alkyl)amino or diarylamino, and $R^3$ signifies hydrogen, $C_{1-6}$-alkyl, ($C_{1-6}$-alkyl)carbonyl, aroyl, ($C_{1-6}$-alkoxy)carbonyl, tri-($C_{1-6}$-alkyl)silyl, di($C_{1-6}$-alkyl)phosphonyl, diarylphosphonyl, ($C_{1-6}$-alkyl)sulphonyl or arylsulphonyl, with the proviso that in the case of the pentadiene derivatives of the formula IIa, when $R^1$ signifies hydroxyl, $R^2$ cannot signify arylsulphonyl.

13. A process according to claim 2, wherein the Lewis acid is selected from the group consisting of zinc chloride, zinc chloride dietherate, zinc bromide, zinc di(trifluoromethanesulphonate), titanium tetrachloride, tin tetrachloride, boron trifluoride etherate, iron(III) chloride, trimethylsilyl triflate and lithium perchlorate and the Brönsted acid is selected from the group consisting of p-toluenesulphonic acid, methanesulphonic acid, trifluoromethanesulphonic acid, sulphuric acid and trifluoroacetic acid.

14. A process according to claim 13, wherein a Lewis acid is selected from the group consisting of the named zinc salts, boron trifluoride etherate and iron(III) chloride.

15. A process according to claim 5 wherein the wherein the Lewis or Brönsted acid is used in a catalytic amount which is 1 to 15 mol percent, based on the amount of 5-substituted pent(adi)en(yn)e derivative of the formula IIa, IIb, IIc, IId or IIe used.

16. A process according to claim 6 wherein 1.1 to 1.8 equivalents of 1,3-butadiene derivative of the formula III are used per equivalent of 5-substituted pent(adi)en(yn)e derivative of the formula IIa, IIb, IIc, IId or IIe.

17. A process according to claim 7 wherein the temperature range is from about −30° to room temperature.

18. A process according to claim 7 wherein the lower halogenated aliphatic hydrocarbon is methylene chloride or chloroform; the lower aliphatic or cyclic ether is diethyl ether, tert.butyl methyl ether or tetrahydrofuran; the lower aliphatic nitrile is acetonitrile; the lower aliphatic ester is ethyl acetate; the lower aliphatic hydrocarbon is pentane or hexane; and the aromatic hydrocarbon is toluene.

19. A process according to claim 8 wherein the alkali metal alcoholate is sodium ethylate; the nitrogen-containing base is 1,8-diazabicyclo[5.4.0]undec-7-ene; the trialkylamine is trimethylamine or pyridine; the strong mineral acid is hydrochloric acid, hydrobromic acid, hydriodic acid, sulphuric acid or perchloric acid; and the sulphonic acid is methanesulphonic acid, trifluoromethanesulphonic acid or p-toluenesulphonic acid.

20. A process according to claim 10, wherein the so obtained (all-E)-retinal-hydroquinone adduct is converted to vitamin A alcohol in the predominantly (all-E)-isomeric form by known methods.

* * * * *